United States Patent [19]

Pastan

[11] Patent Number: 5,489,525
[45] Date of Patent: Feb. 6, 1996

[54] MONOCLONAL ANTIBODIES TO PROSTATE CELLS

[75] Inventor: Ira H. Pastan, Potomac, Md.

[73] Assignee: The United States of America as represented by the Department of Health and Human Services, Washington, D.C.

[21] Appl. No.: 958,140

[22] Filed: Oct. 8, 1992

[51] Int. Cl.$^6$ .......................... G01N 33/53; G01N 33/574
[52] U.S. Cl. .................... 435/7.23; 435/7.9; 435/240.27; 436/64; 436/813; 424/1.49; 530/387.9; 530/388.8; 530/388.85; 530/389.7
[58] Field of Search .................................... 435/7.23, 7.9, 435/240.27; 424/9; 436/64, 813; 530/387.7, 388.8, 388.85, 389.7

[56] References Cited

U.S. PATENT DOCUMENTS

| | | | |
|---|---|---|---|
| 4,444,744 | 4/1984 | Goldenberg | 424/1.1 |
| 4,970,299 | 11/1990 | Bazinet et al. | 530/387 |
| 5,055,404 | 10/1991 | Udea et al. | 435/240 |

FOREIGN PATENT DOCUMENTS

| | | |
|---|---|---|
| 8101849 | 7/1981 | WIPO . |
| 9207271 | 4/1992 | WIPO . |

OTHER PUBLICATIONS

Starling, et al., *Cancer Res.*, vol. 46, pp. 367–374, Jan. 1986.
*Monoclonal Antibody Technology*, A. M. Campbell, Elsevier, New York, pp. 98–100, 1987.
Lowe, D. H., et al., *J. Urol.* 132(4) pp. 780–785, "A Human Monoclonal Antibody Reactive with Human Prostate" 1984.
Brinkman et al., "A Recombinant Immunotoxin that is Active on Prostate Cancer Cells and that is Composed of the Fv Region of Monoclonal Antibody PR1 and a Truncated Form of Pseudomonas Exotoxin" *Proc. Natl. Acad. Sci. USA* 90:547–551 (Jan., 1993).
Pastan et al., "PR1—A Monoclonal Antibody That Reacts With an Antigen of the Surface of Normal and Malignant Prostate Cells", *J. Nat'l. Can. Inst.* 85(14):1149–1154 (Jul. 21, 1993).
Sablitzky et al., "Molecular Basis of an Isogeneic Anti-Idiotypic Response", *EMBO J.* 3: 3005–3012 (1984).
Starling et al., "Disulfide Bonding of a Human Prostate Tumor–associated Membrane Antigen Recognized by Monoclonal Antibody D83.21", *Cancer Res.* 45:804–808 (Feb., 1985).
Peehl, "Serial Culture of Adult Human Prostatic Epithelial Cells", *J. Tiss. Cult. Meths.* 9:53–60 (1985).
Peehl et al., "Serum–Free Growth of Adult Human Prostatic Epithelial Cells", *In Vitro* 22:82–90 (Feb., 1986).
Horoszewicz et al., "Monoclonal Antibodies to a New Antigenic Marker in Epithelial Prostatic Cells and Serum of Prostatic Cancer Patients", *Anticancer Res.* 7: 927–936 (1987).
Kim et al., "Monoclonal Antibody PR92 with Restricted Specificity for Tumor–associated Antigen of Prostate and Breast Carcinoma", *Cancer Res.* 48:4543–4548 (Aug. 15, 1988).
Bazinet et al., "Immunohistochemical Characterization of Two Monoclonal Antibodies, P25,48 and P25.91, Which Define a New Prostate–specific Antigen", *Cancer Res.* 48:6938–6942 (Dec. 1988).
Lee et al., "Experimental Immunochemotherapy of Human Prostate Tumor with 5-Fluorodeoxyuridine Monoclonal Anti–Prostate Acid Phosphatase Antibody Conjugate", *J. Tumor Marker Oncol.* 3: 361–372 (1988).
De Boer "Symmetric Idiotypic Networks: Connectance & Switching, Stability, and Suppression", *Theoretical Immunology, Pt. Two*, A. S. Perelson, ed., pp. 265–289 (1988) Addison Wesley Pub. Co.
Lopes et al., "Immunohistochemical and Pharmacokinetic Characterization of the Site–specific Immunoconjugate CYT–356 Derived from Antiprostate Monoclonal Antibody 7E11–C5", *Cancer Res.* 50:6423–6429 (Oct. 1, 1990).
Wright et al., "Radiolocalization of Human Prostate Tumor in a Mouse Subrenal Capsule Model by Monoclonal Antibody TURP–27", *The Prostate* 16: 81–89 (1990).
Beckett et al. "Monoclonal Antibody PD41 Recognizes an Antigen Restricted to Prostate Adenocarcinomas", *Cancer Res.* 51:1326–1333 (Feb. 15, 1991).
Lipford et al., "Comparative Study of Monoclonal Antibodies TURP–27 and HNK–1: Their Relationship to Neural Cell Adhesion Molecules and Prostate Tumor–associated Antigens", *Cancer Res.* 51: 2296–2301 (May 1, 1991).
Pastan et al., "Characterization of Monoclonal Antibodies B1 & B3 that React with Mucinous Adenocarcinomas", *Cancer Res.* 51:3784–3787 (Jul. 15, 1991).
Tjota et al., "Murine Monoclonal Antibodies Reactive with a Variety of Androgen Independent Dunning Rat Prostate Adenocarcinoma Sublines Also Reactive with Human Prostate Adenocarcinoma", *J. Urol.* 146: 205–212 (Jul., 1991).
Brinkmann et al., "B3(Fv)–PE38KDEL, a Single–Chain Immunotoxin that Causes Complete Regression of a Human Carcinoma in Mice," *Proc. Natl. Acad. Sci. USA* 88:8616–8620 (Oct., 1991).
Gansow, "Newer Approaches to the Radiolabeling of Monoclonal Antibodies by Use of Metal Chelates", *Int. J. Rad Appl. Instrum.* [B], *Nucl. Med. Biol.* 18:369–381 (1991).
Peehl et al. "Culture of Prostatic Epithelial Cells from Ultrasound–Guided Needle Biopsies", *The Prostate* 19:141–147 (1991).
Wright et al., "A Novel Prostate Carcinoma–associated Glycoprotein Complex (PAC) Recognized by Monoclonal Antibody TURP–27", *Int. J. Cancer* 47: 717–725 (1991).

(List continued on next page.)

*Primary Examiner*—Toni R. Scheiner
*Attorney, Agent, or Firm*—Townsend and Townsend Khourie and Crew

[57] ABSTRACT

Monoclonal antibodies are provided which bind to an antigen associated with prostate cells, including prostate cancers. The monoclonal antibodies and recombinant forms thereof are used individually or conjugated radioisotopes to target the compounds to cancerous prostate cells, and thus are useful in a variety of diagnostic procedures.

11 Claims, 6 Drawing Sheets

OTHER PUBLICATIONS

Brinkmann et al., "Independent Domain Folding of Pseudomonas Exotoxin & Single–Chain Immunotoxins: Influence of Interdomain Connections" *Proc. Natl. Acad. Sci. USA* 89:3075–3079 (Apr. 1992).

Chang et al., "Isolation and Characterization of a Monoclonal Antibody, K1, Reactive with Ovarian Cancers and Normal Mesothelium" *Int. J. Cancer* 50: 373–381 (1992).

Chang et al., "Frequent Expression of the Tumor Antigen CAK1 in Squamous–cell Carcinomas" *Int. J. Cancer* 51: 548–554 (1992).

Chang et al., "Monoclonal Antibody K1 Reacts with Epithelia Mesothelioma But Not With Lung Adenocarcinoma", *Amer J. Surg. Pathol.* 16: 258–268 (1992).

```
            --SD--        NdeI  |----------V_H---------------
  1 TTAACTCTAAGAAGGAGATATACATATGGATGTGCAGCTGGTGGAGTCTGGAGG
                                 M  D  V  Q  L  V  E  S  G  G
    -->
 55 TGGCCTGGTGCAGCCTGGAGGATCCCTGAAACTCTCCTGTGCAGCCTCAGGATT
     G  L  V  Q  P  G  G  S  L  K  L  S  C  A  A  S  G  F

109 CGATTTTAGTAGATACTGGATGAGTTGGGTCCGGCAGGCTCCAGGGAAAGGGCT
     D  F  S  R  Y  W  M  S  W  V  R  Q  A  P  G  K  G  L

163 AGAATGGATTGGAGAAATTAATCCAGATAGCAGTACGATAAACTATACGCCATC
     E  W  I  G  E  I  N  P  D  S  S  T  I  N  Y  T  P  S

217 TCTAAAGGATAAATTCATCATCTCCAGTGACAACGCCAAAAATACGCTGTACCT
     L  K  D  K  F  I  I  S  S  D  N  A  K  N  T  L  Y  L

271 GCAAATGAGCAAAGTGAGATCTGAGGACACAGCCCTTTATTACTGTGCAAGACG
     Q  M  S  K  V  R  S  E  D  T  A  L  Y  Y  C  A  R  R

325 GGGGTACTATGCTATGGACTACTGGGGTCAAGGAACCTCAGTCACCGTCTCCTC
     G  Y  Y  A  M  D  Y  W  G  Q  G  T  S  V  T  V  S  S
                                       ------V_H----------

379 AGGCGGAGGGGGATCCGGTGGTGGCGGATCTGGAGGTGGCGGCAGCGACATTGT
     G  G  G  G  S  G  G  G  G  S  G  G  G  G  S  D  I  V
                                                    D  I  Q
    ||----------------LINKER----------------------|| |-------

433 GATGACCCAGTCTCCAGCCTCCCTATCTGCATCTGTGGGAGAAACTGTCACCAT
     M  T  Q  S  P  A  S  L  S  A  S  V  G  E  T  V  T  I
     M  T  Q  S  P  A  S  L  S  A
    ----------------------------V_L----------------------->

487 CACATGTCGAGCAAGTGAGAATATTTACAGTTATTTAGCATGGTATCAGCAGAA
     T  C  R  A  S  E  N  I  Y  S  Y  L  A  W  Y  Q  Q  K

541 ACAGGGAAAATCTCCTCAGCTCCTGGTCTATAATGCAAAAACCTTAGCAGAAGG
     Q  G  K  S  P  Q  L  L  V  Y  N  A  K  T  L  A  E  G

595 TGTGCCATCAAGGTTCAGTGGCAGTGGATCAGGCACACAGTTTTCTCTGAAGAT
     V  P  S  R  F  S  G  S  G  S  G  T  Q  F  S  L  K  I
```

FIG. 1A-1.

```
649 CAACAGCCTGCAGCCTGAAGATTTTGGGAGTTATTACTGTCAACATCATTATGG
     N  S  L  Q  P  E  D  F  G  S  Y  Y  C  Q  H  H  Y  G

703 TACTCCATTCACGTTCGGCTCGGGCACAAAGCTGGAAATAAAAGCTTCCGGA-
     T  P  F  T  F  G  S  G  T  K  L  E  I  K  A  S  G
                    --------V_L------------  HindIII

- - - - PE38KDEL - - - →
```

FIG. 1A-2.

```
DVQLVESGGGLVQPGGSLKLSCAASGFDFSRYWMSWVRQAPGKGLEWIGEINPDSSTI
:| | :|||||||||||||:||||||||||||||||||||||||||||||||||||
QVKLKQSGGGLVQPGGSLKVSCAASGFDFSRYWMSWVRQAPGKGLEWIGEINPDSSTI

NYTPSLKDKFIISSDNAKNTLYLQMSKVRSEDTALYYCARRGYYA.......MDYWGQ
 |||||||||:| ||||||||| ||||| |||||||||           | ||
IYTPSLKDKFIMSRDNAKNTLYLQTSKVRSADTALYYCARRGSHYYGYRTGYFDVWGA

GTSVTVSS
|| |||||
GTTVTVSS
```

FIG. 1B.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 754 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 26..754

( x i ) SEQUENCE DESCRIPTION: SEQ ID NO:1:

```
TTAACTCTAA GAAGGAGATA TACAT ATG GAT GTG CAG CTG GTG GAG TCT GGA              52
                              Met Asp Val Gln Leu Val Glu Ser Gly
                               1               5

GGT GGC CTG GTG CAG CCT GGA GGA TCC CTG AAA CTC TCC TGT GCA GCC             100
Gly Gly Leu Val Gln Pro Gly Gly Ser Leu Lys Leu Ser Cys Ala Ala
 10              15                  20                  25

TCA GGA TTC GAT TTT AGT AGA TAC TGG ATG AGT TGG GTC CGG CAG GCT             148
Ser Gly Phe Asp Phe Ser Arg Tyr Trp Met Ser Trp Val Arg Gln Ala
             30                  35                  40

CCA GGG AAA GGG CTA GAA TGG ATT GGA GAA ATT AAT CCA GAT AGC AGT             196
Pro Gly Lys Gly Leu Glu Trp Ile Gly Glu Ile Asn Pro Asp Ser Ser
             45                  50                  55

ACG ATA AAC TAT ACG CCA TCT CTA AAG GAT AAA TTC ATC ATC TCC AGT             244
Thr Ile Asn Tyr Thr Pro Ser Leu Lys Asp Lys Phe Ile Ile Ser Ser
         60                  65                  70

GAC AAC GCC AAA AAT ACG CTG TAC CTG CAA ATG AGC AAA GTG AGA TCT             292
```

```
                Asp  Asn  Ala  Lys  Asn  Thr  Leu  Tyr  Leu  Gln  Met  Ser  Lys  Val  Arg  Ser
                      75                  80                       85

GAG  GAC  ACA  GCC  CTT  TAT  TAC  TGT  GCA  AGA  CGG  GGG  TAC  TAT  GCT  ATG                340
Glu  Asp  Thr  Ala  Leu  Tyr  Tyr  Cys  Ala  Arg  Arg  Gly  Tyr  Tyr  Ala  Met
 90                  95                      100                       105

GAC  TAC  TGG  GGT  CAA  GGA  ACC  TCA  GTC  ACC  GTC  TCC  TCA  GGC  GGA  GGG                388
Asp  Tyr  Trp  Gly  Gln  Gly  Thr  Ser  Val  Thr  Val  Ser  Ser  Gly  Gly  Gly
                     110                      115                      120

GGA  TCC  GGT  GGT  GGC  GGA  TCT  GGA  GGT  GGC  GGC  AGC  GAC  ATT  GTG  ATG                436
Gly  Ser  Gly  Gly  Gly  Gly  Ser  Gly  Gly  Gly  Gly  Ser  Asp  Ile  Val  Met
               125                      130                      135

ACC  CAG  TCT  CCA  GCC  TCC  CTA  TCT  GCA  TCT  GTG  GGA  GAA  ACT  GTC  ACC                484
Thr  Gln  Ser  Pro  Ala  Ser  Leu  Ser  Ala  Ser  Val  Gly  Glu  Thr  Val  Thr
               140                      145                      150

ATC  ACA  TGT  CGA  GCA  AGT  GAG  AAT  ATT  TAC  AGT  TAT  TTA  GCA  TGG  TAT                532
Ile  Thr  Cys  Arg  Ala  Ser  Glu  Asn  Ile  Tyr  Ser  Tyr  Leu  Ala  Trp  Tyr
          155                      160                      165

CAG  CAG  AAA  CAG  GGA  AAA  TCT  CCT  CAG  CTC  CTG  GTC  TAT  AAT  GCA  AAA                580
Gln  Gln  Lys  Gln  Gly  Lys  Ser  Pro  Gln  Leu  Leu  Val  Tyr  Asn  Ala  Lys
170                      175                      180                      185

ACC  TTA  GCA  GAA  GGT  GTG  CCA  TCA  AGG  TTC  AGT  GGC  AGT  GGA  TCA  GGC                628
Thr  Leu  Ala  Glu  Gly  Val  Pro  Ser  Arg  Phe  Ser  Gly  Ser  Gly  Ser  Gly
                    190                      195                      200

ACA  CAG  TTT  TCT  CTG  AAG  ATC  AAC  AGC  CTG  CAG  CCT  GAA  GAT  TTT  GGG                676
Thr  Gln  Phe  Ser  Leu  Lys  Ile  Asn  Ser  Leu  Gln  Pro  Glu  Asp  Phe  Gly
               205                      210                      215

AGT  TAT  TAC  TGT  CAA  CAT  CAT  TAT  GGT  ACT  CCA  TTC  ACG  TTC  GGC  TCG                724
Ser  Tyr  Tyr  Cys  Gln  His  His  Tyr  Gly  Thr  Pro  Phe  Thr  Phe  Gly  Ser
          220                      225                      230

GGC  ACA  AAG  CTG  GAA  ATA  AAA  GCT  TCC  GGA                                               754
Gly  Thr  Lys  Leu  Glu  Ile  Lys  Ala  Ser  Gly
          235                      240
```

( 2 ) INFORMATION FOR SEQ ID NO:2:

( i ) SEQUENCE CHARACTERISTICS:
        ( A ) LENGTH: 243 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Val  Gln  Leu  Val  Glu  Ser  Gly  Gly  Gly  Leu  Val  Gln  Pro  Gly
 1                   5                      10                       15

Gly  Ser  Leu  Lys  Leu  Ser  Cys  Ala  Ala  Ser  Gly  Phe  Asp  Phe  Ser  Arg
               20                      25                       30

Tyr  Trp  Met  Ser  Trp  Val  Arg  Gln  Ala  Pro  Gly  Lys  Gly  Leu  Glu  Trp
          35                      40                       45

Ile  Gly  Glu  Ile  Asn  Pro  Asp  Ser  Ser  Thr  Ile  Asn  Tyr  Thr  Pro  Ser
     50                      55                       60

Leu  Lys  Asp  Lys  Phe  Ile  Ile  Ser  Ser  Asp  Asn  Ala  Lys  Asn  Thr  Leu
 65                      70                       75                       80

Tyr  Leu  Gln  Met  Ser  Lys  Val  Arg  Ser  Glu  Asp  Thr  Ala  Leu  Tyr  Tyr
                85                      90                       95

Cys  Ala  Arg  Arg  Gly  Tyr  Tyr  Ala  Met  Asp  Tyr  Trp  Gly  Gln  Gly  Thr
               100                      105                      110

Ser  Val  Thr  Val  Ser  Ser  Gly  Gly  Gly  Gly  Ser  Gly  Gly  Gly  Gly  Ser
          115                      120                      125

Gly  Gly  Gly  Gly  Ser  Asp  Ile  Val  Met  Thr  Gln  Ser  Pro  Ala  Ser  Leu
```

```
              130                    135                    140
Ser  Ala  Ser  Val  Gly  Glu  Thr  Val  Thr  Ile  Thr  Cys  Arg  Ala  Ser  Glu
145                      150                      155                      160

Asn  Ile  Tyr  Ser  Tyr  Leu  Ala  Trp  Tyr  Gln  Gln  Lys  Gln  Gly  Lys  Ser
                    165                      170                      175

Pro  Gln  Leu  Leu  Val  Tyr  Asn  Ala  Lys  Thr  Leu  Ala  Glu  Gly  Val  Pro
               180                      185                      190

Ser  Arg  Phe  Ser  Gly  Ser  Gly  Ser  Gly  Thr  Gln  Phe  Ser  Leu  Lys  Ile
          195                      200                      205

Asn  Ser  Leu  Gln  Pro  Glu  Asp  Phe  Gly  Ser  Tyr  Tyr  Cys  Gln  His  His
     210                      215                      220

Tyr  Gly  Thr  Pro  Phe  Thr  Phe  Gly  Ser  Gly  Thr  Lys  Leu  Glu  Ile  Lys
225                      230                      235                      240

Ala  Ser  Gly
```

( 2 ) INFORMATION FOR SEQ ID NO:3:

( i ) SEQUENCE CHARACTERISTICS:
        ( A ) LENGTH: 117 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

```
Asp  Val  Gln  Leu  Val  Glu  Ser  Gly  Gly  Gly  Leu  Val  Gln  Pro  Gly  Gly
1                        5                        10                       15

Ser  Leu  Lys  Leu  Ser  Cys  Ala  Ala  Ser  Gly  Phe  Asp  Phe  Ser  Arg  Tyr
               20                       25                       30

Trp  Met  Ser  Trp  Val  Arg  Gln  Ala  Pro  Gly  Lys  Gly  Leu  Glu  Trp  Ile
          35                       40                       45

Gly  Glu  Ile  Asn  Pro  Asp  Ser  Ser  Thr  Ile  Asn  Tyr  Thr  Pro  Ser  Leu
     50                       55                       60

Lys  Asp  Lys  Phe  Ile  Ile  Ser  Ser  Asp  Asn  Ala  Lys  Asn  Thr  Leu  Tyr
65                       70                       75                       80

Leu  Gln  Met  Ser  Lys  Val  Arg  Ser  Glu  Asp  Thr  Ala  Leu  Tyr  Tyr  Cys
                    85                       90                       95

Ala  Arg  Arg  Gly  Tyr  Tyr  Ala  Met  Asp  Tyr  Trp  Gly  Gln  Gly  Thr  Ser
               100                      105                      110

Val  Thr  Val  Ser  Ser
               115
```

( 2 ) INFORMATION FOR SEQ ID NO:4:

( i ) SEQUENCE CHARACTERISTICS:
        ( A ) LENGTH: 124 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

```
Gln  Val  Lys  Leu  Lys  Gln  Ser  Gly  Gly  Gly  Leu  Val  Gln  Pro  Gly  Gly
1                        5                        10                       15

Ser  Leu  Lys  Val  Ser  Cys  Ala  Ala  Ser  Gly  Phe  Asp  Phe  Ser  Arg  Tyr
               20                       25                       30

Trp  Met  Ser  Trp  Val  Arg  Gln  Ala  Pro  Gly  Lys  Gly  Leu  Glu  Trp  Ile
          35                       40                       45
```

```
        Gly  Glu  Ile  Asn  Pro  Asp  Ser  Ser  Thr  Ile  Ile  Tyr  Thr  Pro  Ser  Leu
              50                  55                            60

Lys  Asp  Lys  Phe  Ile  Met  Ser  Arg  Asp  Asn  Ala  Lys  Asn  Thr  Leu  Tyr
        65                       70                       75                       80

Leu  Gln  Thr  Ser  Lys  Val  Arg  Ser  Ala  Asp  Thr  Ala  Leu  Tyr  Tyr  Cys
                             85                       90                        95

Ala  Arg  Arg  Gly  Ser  His  Tyr  Tyr  Gly  Tyr  Arg  Thr  Gly  Tyr  Phe  Asp
                       100                      105                      110

Val  Trp  Gly  Ala  Gly  Thr  Thr  Val  Thr  Val  Ser  Ser
                  115                      120
```

( 2 ) INFORMATION FOR SEQ ID NO:5:

( i ) SEQUENCE CHARACTERISTICS:
        ( A ) LENGTH: 46 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
CAGTRDCTRM  AGGTGTCCAT  ATGGATGTGC  AGCTGGTGGA  GTCTGG                       46
```

( 2 ) INFORMATION FOR SEQ ID NO:6:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
GGAGACAAGC  TTGAAGACAT  TTGGGAAGGA  CTGACTC                                  37
```

( 2 ) INFORMATION FOR SEQ ID NO:7:

( i ) SEQUENCE CHARACTERISTICS:
        ( A ) LENGTH: 77 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

```
GTCTCCTCAG  GCGGAGGGGG  ATCCGGTGGT  GGCGGATCTG  GAGGKGGCGG  MAGCGAHRTT       60

GTGATGACCC  AGTCTCC                                                          77
```

( 2 ) INFORMATION FOR SEQ ID NO:8:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

```
AGTTGGTGCA  GCATCAAAAG  CTTTKAKYTC  CAGCYTKGTG  CC                           42
```

( 2 ) INFORMATION FOR SEQ ID NO:9:

( i ) SEQUENCE CHARACTERISTICS:
   ( A ) LENGTH: 40 base pairs
   ( B ) TYPE: nucleic acid
   ( C ) STRANDEDNESS: single
   ( D ) TOPOLOGY: linear ( i i ) MOLECULE TYPE: cDNA ( x i ) SEQUENCE DESCRIPTION: SEQ ID NO:9:

GGATCCCCCT CCGCCTGAGG AGACGGTGAC TGAGGTTCCT                40

( 2 ) INFORMATION FOR SEQ ID NO:10:

( i ) SEQUENCE CHARACTERISTICS:
      ( A ) LENGTH: 13 amino acids
      ( B ) TYPE: amino acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:10:

Asp Ile Gln Met Thr Gln Ser Pro Ala Ser Leu Ser Ala
   1               5                   10

( 2 ) INFORMATION FOR SEQ ID NO:11:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( x i ) SEQUENCE DESCRIPTION: SEQ ID NO:11:

CATTTGGGAA GGACTGACTC                                      20

MONOCLONAL ANTIBODIES TO PROSTATE CELLS

BACKGROUND OF THE INVENTION

Prostate cancer will soon become the leading cause of cancer death of men in the United States. One-third of men over 50 will develop prostate cancer at some time in their lives. In 1992, nearly 132,000 men will be diagnosed as having prostate cancer, and 34,000 are likely to die from the disease. With the aging U.S. population, it has been estimated that prostate cancer cases will increase 90% and deaths will increase 37% by the end of the decade.

There are two main types of prostate cancer: sarcoma, a rare, highly malignant and fast growing tumor; and adenocarcinoma, a slower growing type which comprises 95% of prostate cancers. Adenocarcinoma is often devoid of symptoms in its early stages, when it is most susceptible to treatment. Unfortunately, 40% of adenocarcinomas are detected at an advanced stage.

Among the methods employed for detection of prostate cancer, the digital rectal exam is the oldest and simplest, but in 70% of patients the exam fails to reveal cancer until it has spread to other parts of the body. Because of the high miss rate, such exams are now being used in conjunction with a blood test for prostate specific antigen (PSA), which was first isolated in 1979. PSA is recognized as the best tumor marker presently available, being more sensitive and more specific than either the rectal exam or the prostatic acid phosphatase test. The PSA protein is made and secreted by both normal and cancerous prostate cells, but is elevated in the blood of men with prostate cancer. The older prostatic acid phosphatase (PAP) test has been displaced by the PSA assay, although it remains a tool for monitoring metastases and response to therapy, especially endocrine treatment.

Once diagnosed, there are three basic treatment options for prostate cancer: surgery, radiation and endocrine therapy. Prostate cancer is resistant to most of the commonly used anticancer drugs, including cisplatin, adriamycin and cyclophosphamide. The choice of treatment depends primarily on the stage of the disease. As with other solid tumors, surgery is preferred when it is feasible. If pelvic lymph nodes reveal cancerous invasion, radical surgery or radiation are of little use.

Endocrine therapy, including diminishing the levels of testosterone by orchiectomy, is generally reserved for metastatic cancer and is not curative but only a means of slowing the progress of the disease. Prostatic carcinomas usually further metastasize to bone, where they are inaccessible to surgery and may be extremely painful to the patient.

New approaches to the treatment and diagnosis of prostate cancer are clearly and urgently needed. While the PSA protein is a useful diagnostic marker, antibodies to PSA are not useful for therapy or imaging of prostate cancer metastases because the antigen is not a cell membrane protein. Monoclonal antibodies have been isolated that react with normal prostate cells, malignant prostate cells or proteins present in prostate secretions (1–8). Monoclonal antibodies P25.48 (Bazinet et al., Cancer Res. 48:6938–6942 (1988)), P25.91 (Bazinet et al., Cancer Res. 48:6938–6942 (1988)), MCA/R1 and LSD 83/21 (Starling and Wright, Cancer Res. 45:804– 808 (1985)) do not react at all with normal prostate cells, and monoclonal antibody PD41 (Beckett, Cancer Res. 51:1326– 1333 (1991)) reacts with less than 1% of epithelial cells in normal prostate. Antibodies HNK-1 and TURP-27 recognize neural cell adhesion molecules that are also expressed in normal prostate. However, these antibodies only react with scattered cells in the normal prostate epithelium. In addition, monoclonal antibodies HNK-1 and TURP-27 react with normal brain tissue. Monoclonal antibody PR92 was produced by immunizing with cells from a long established prostate cell line, DU145 cells, with which it strongly reacts (Kim et al., Cancer Res. 48:4543–4548 (1988)). The DU145 cells may lack certain antigens characteristic of prostate cells. Horoszewicz et al. (Anticancer Res. 7:927–936 (1987)) have developed a monoclonal antibody (7E11-C5) to prostate cancer cells by immunizing mice with the cell line LNCaP. This antibody, however, reacts uniformly with LNCaP cells and skeletal and cardiac muscle (Horoszewicz et al., ibid., and Lopes et al., Cancer Res. 50:6423–6429 (1990)).

Quite surprisingly, the present invention provides a novel approach to solving the need for improved treatment and diagnosis of prostate cancer, and fulfills other related needs.

SUMMARY OF THE INVENTION

The present invention provides monoclonal antibodies and binding fragments thereof which are capable of binding to an antigen specific for prostate cells, including prostate adenocarcinomas and other prostate cancer cells. In a preferred embodiment the monoclonal antibody is PR1 as described herein or competes with monoclonal antibody PR1 for binding to the prostate cell associated antigen. Chimeric and other forms of recombinant antibodies may be made which have the binding specificity of the monoclonal antibodies of the invention, including single polypeptide chain binding molecules, which may themselves be bound to other molecules for therapeutic and diagnostic purposes. For administration to humans, the antibodies are preferably substantially human, and may be linked to a toxin, such as Pseudomonas exotoxin A, drug, or radioisotope. Preferably the antibody will be of the IgG isotype, and may even be linked to itself to form an IgG homodimer having increased activity against tumors.

In other embodiments the invention provides methods for targeting a drug useful in the treatment of prostate cancer to prostate cells of a patient suffering from the disease. The cells of the patient are exposed in vivo or ex vivo to a therapeutically effective amount of said drug linked to a monoclonal antibody or binding fragment thereof such as PR1 which competes with monoclonal antibody PR1 for binding to the prostate cell associated antigen. The administration of the monoclonal antibodies of the invention may also be used in methods for diagnosing the presence of prostate cancer in an individual, or for guiding surgical removal of metastatic prostate cells.

BRIEF DESCRIPTION OF THE FIGURES

FIGS. 1A-1, 1A-2 and 1B are the nucleotide sequences encoding the heavy- and light-chain variable region of monoclonal antibody PR1. (A) The $V_H$ coding sequence extends from position 29 to 375, $V_L$ from 426 to 743. The deduced amino acid sequence is shown in capitals, the amino acid sequence determined by Edman sequencing of the light chain below in italic letters. A difference at position 440 between the protein sequence of the PR1 kappa chain and the cloned sequence is due to the primer L1 that was used for PCR. The $V_H$ sequence was confirmed by RNA sequencing. (B) Similarity between the heavy chain variable regions of monoclonal antibody PR1 and monoclonal antibody K1.

FIG. 2A is the plasmid pUL140 for expression of PR1(Fv)-PE38KDEL, and FIG. B is the Coomassie Blue-stained reducing SDS-PAGE on 12.5% polyacrylamide gel, the lanes showing (a) total protein of cells producing PR1(Fv)-PE38KDEL, (b) supernatant of sonicated cells, (c) inclusion bodies, and (d) immunotoxin after renaturation, ion exchange chromatography and gel filtration. The molecular weight standards (M) are indicated on the left, $\times 10^{-3}$.

DESCRIPTION OF THE SPECIFIC EMBODIMENTS

Figure 2A:
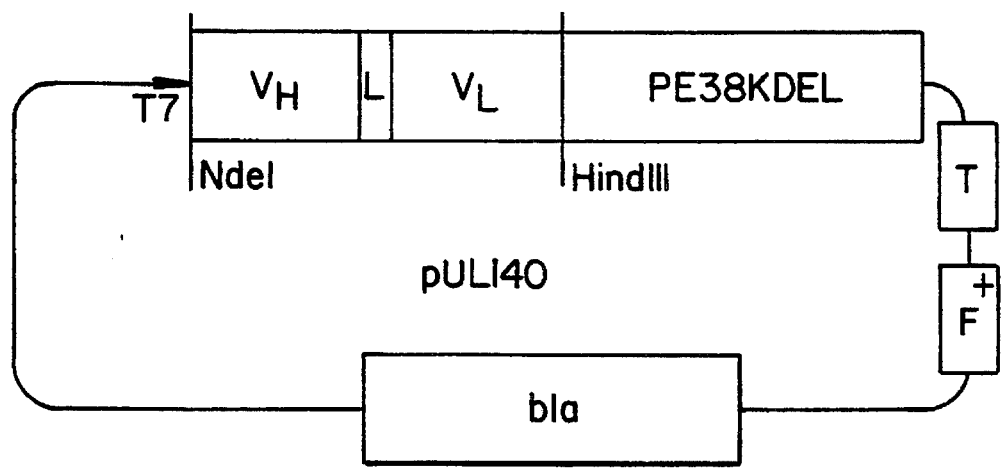
FIGS. 2A and 2B show the expression and purification of the recombinant immunotoxin PR1(Fv)-PE38KDEL, where

The present invention provides monoclonal antibodies useful in the therapy and diagnosis of prostate cancer. Monoclonal antibodies are provided that recognize a differentiation antigen present on the surface of normal prostate cells that is also expressed on cancerous prostate cells. Accordingly, methods of therapy can be employed with the present invention which destroys prostate cancer cells. The effect of the therapy on normal prostate cells does not threaten the overall health of the patient.

The monoclonal antibodies described herein react strongly with the surface of normal prostate cells and with the great majority of adenocarcinomas of the prostate. The monoclonal antibodies react very weakly with a few other normal human tissues. However, because the reactivity with prostate cancer cells is very strong, these monoclonal antibodies are useful in the diagnosis and treatment of prostate cancer in a variety of ways not heretofore possible.

The monoclonal antibodies of the invention, as exemplified by monoclonal antibody PR1, react with a differentiation antigen on prostate cells that continues to be expressed in almost all adenocarcinomas of the prostate. The representative PR1 monoclonal antibody reacts with 25/26 primary prostate carcinoma samples that have been examined, which range from well differentiated carcinomas to those which are poorly differentiated. In addition, PR1 reacts with two metastatic prostate cancers, one located in a lymph node and the other in the bladder.

The antigen recognized by the monoclonal antibodies of the invention is associated with the plasma membrane of normal prostate epithelial cells and adenocarcinomas of the prostate. The monoclonal antibodies to said antigen do not react with prostate secretions. Another distinguishing feature of the monoclonal antibodies are a uniform and strong reactivity with almost all cells of adenocarcinomas of the prostate.

Prostate cell antigen recognized by the PR1 monoclonal antibody may be purified, e.g., by immunoaffinity purification using the PR1 antibody, and used to immunize animals to produce additional monoclonal antibodies of the invention. Alternatively, animals may be immunized with prostate cells or preparations thereof which express the antigen. The three existing prostate carcinoma cell lines, DU145 (ATCC HTB 81), LNCaP (ATCC CRL 1740), and PC-3 (ATCC CRL 1435), may be atypical in antigens which they express, and other prostate cancer cell lines have been difficult to establish. Therefore, according to the present invention short term prostate cell lines are used to immunize animals, preferably mice, for the subsequent production of monoclonal antibody secreting cell lines. This method differs from procedures typically used to identify monoclonal antibodies to prostate antigens, such as immunizing mice with one of the three existing prostate carcinoma cell lines, with tissue from patient samples, or with purified soluble proteins secreted by prostate cells. The short term prostate cell lines have been found to generally retain the characteristics of the prostate cancers or normal prostate cells from which they are derived.

In addition to the lack of suitable cells or antigens for immunization, it has also been difficult in the past to prepare sufficient numbers of cells for immunization or for screening the resulting hybridomas which are produced using cells obtained from the immunized animals. As described herein, a fluorescence screening chamber can be employed (e.g., Screen Fast) to rapidly screen many hybridomas using a limited number of cells from the short term prostate lines to identify the monoclonal antibodies that react strongly and uniformly with the surface of the prostate cells. This screening process efficiently eliminates monoclonal antibodies that react with secreted prostate cell antigens such as PSA, antigens on the extracellular matrix and antigens expressed on only a small fraction of the prostate cells used in the screening.

The monoclonal antibody-producing cell lines of the invention may be isolated from B cells of several species using conventional fusion, viral transformation or other immortalization techniques well known to those skilled in the art, in conjunction with the screening procedures described herein. While rodent, particularly murine monoclonal antibodies are conveniently produced, B cells from other species may also be employed, such as lagomorpha, bovine, ovine, equine, porcine, avian (see, e.g., U.S. Pat. No. 5,028,540, incorporated herein by reference) and the like. The monoclonal antibody may be of any of the classes or subclasses of immunoglobulins known for each species of animal, such as IgM, IgD, IgA IgE, or subclasses of IgG.

Thus, the present invention also provides substantially pure monoclonal antibodies to the homologous PR1 prostate cell antigen. Purified preparations of the prostate cell antigen recognized by PR1 is also provided. Purification of the monoclonal antibodies or the prostate cell antigen may be achieved by conventional chemical purification means, such as liquid chromatography, immunoaffinity chromatography, gradient centrifugation, and gel electrophoresis, among others. Methods of protein and carbohydrate purification are known in the art (see generally, Scopes, R., *Protein Purification*, Springer-Verlag, N.Y. (1982), which is incorporated herein by reference) and may be applied to the purification of the monoclonal antibodies and prostate cell antigen recognized thereby. Substantially pure monoclonal antibodies of at least about 50% are preferred, at least about 70–80% more preferred, and 95–99% or more homogeneity most preferred, particularly for pharmaceutical uses. Once purified, partially or to homogeneity, as desired, the monoclonal antibodies or the prostate cell antigen may then be used in therapeutic or diagnostic procedures as described herein, to generate antibodies, including anti-idiotypic antibodies, in assay procedures, etc.

By virtue of having the PR1 monoclonal antibody of the present invention which binds prostate cell associated antigen, other monoclonal antibodies of similar binding specificity can be readily identified. For example, the supernatants of immortalized antibody-secreting cells can be screened in a competition assay with the subject PR1 monoclonal antibody as a means to identify monoclonal antibodies which specifically bind to the same or similar epitope as that identified by the exemplary PR1, or to an epitope which is sufficiently proximal to the epitope bound by PR1 so as to inhibit the binding of PR1 to prostate cells which express the antigen.

The antibodies of the invention which bind to the antigen recognized by PR1 may be polyclonal, in the form of antiserum or monospecific antibodies, such as purified antiserum which has been produced by immunizing animals with the prostate cell associated antigen. Preferably, however, the antibodies will be monoclonal. By "monoclonal antibody" is meant an antibody produced by a clonal, continuous cell line separate from cells which produce antibodies of a different antigen binding specificity. Such monoclonal antibodies are produced in substantially pure form relative to antibodies of other binding specificities and typically at a concentration greater than normally occurring in sera from an unimmunized animal of the species which serves as the B cell source.

For administration to humans, e.g., as a component of a composition for *in vivo* therapy or diagnosis, the monoclonal antibodies are preferably substantially human to minimize immunogenicity, and are in substantially pure form. By "substantially human" is meant that the immunoglobulin portion of the composition generally contains at least about 70% human antibody sequence, preferably at least about 80% human, and most preferably at least about 90–95% or more of a human antibody sequence When referring to "antibody," it will be understood that non-immunoglobulin sequences may optionally be present in the molecule so long as the molecule retains the ability to bind the prostate cell associated antigen that is recognized by the PR1 monoclonal antibody.

As the generation of human monoclonal antibodies to human prostate cell antigen may be difficult with conventional human monoclonal antibody techniques, it may be desirable to transfer antigen binding regions (e.g. the $F(ab')_2$, variable or hypervariable (complementarity determining) regions), of non-human monoclonal antibodies, such as from the murine PR1 monoclonal antibody, to human constant regions (Fc) or framework regions using recombinant DNA techniques, thereby producing substantially human molecules. Such methods are generally known in the art and are described in, for example, U.S. Pat. No. 4,816,397, EP publications 173,494 and 239,400, which are incorporated herein by reference.

Alternatively, one may isolate DNA sequences which code for a human monoclonal antibody or portion thereof that specifically binds to the human prostate cell antigen identified with the PR1 antibody by screening a DNA library from human B cells according to the general protocol outlined by Huse et al., *Science* 246:1275–1281 (1989), and described in WO 90/14430, incorporated herein by reference, and then cloning and amplifying the sequences which encode the antibody (or binding fragment) of the desired specificity.

In yet other embodiments, single chain binding polypeptides may be made which bind to the prostate cell associated antigen. These single chain polypeptides may be produced by cloning and joining the variable regions of the heavy and light chains of a monoclonal antibody which binds to the antigen recognized by PR1. Methods for the production of single chain binding polypeptides are described in detail in, e.g., U.S. Pat. No. 4,946,778, which is incorporated herein by reference.

For expressing a monoclonal antibody of the invention which has been produced by recombinant DNA techniques, the host cell is a eucaryotic or procaryotic cell, preferably a eucaryotic cell and more preferably mammalian. Typically the host cell is capable of providing post-translational modifications to immunoglobulin proteins, including leader sequence removal, correct folding and assembly, glycosylation at correct sites, and secretion of functional antibody from the cell. Lymphocyte lines are preferred hosts, especially those of a B cell lineage. The host cell may be a myeloma line, such as Ag8.653, for example. In an example described below, the host cell was *E. coli* and active single chain polypeptide capable of binding antigen on prostate cells was obtained. The recombinant single chain binding polypeptide expressed in *E. coli* further contained a Pseudomonas exotoxin A molecule and thus possessed cytotoxic activity against the targeted prostate cells.

Transfection of host cells for expression of recombinant immunoglobulin molecule which binds to the antigen recognized by the PR1 monoclonal antibody may be accomplished by a number of means, such as electroporation, calcium phosphate coprecipitation of DNA, DEAE dextran precipitation, protoplast fusion and microinjection. Following transfection the cells are typically incubated for a brief period in nonselective medium and are then transferred to selective medium and observed for proliferation. After a sufficient time for cell outgrowth, the supernatants are screened for immunoglobulin, as described herein.

To facilitate identification and selection of transfectants that express the transfected immunoglobulin genes, a gene that confers a selectable phenotype (a selectable marker) is generally introduced into the cells along with the immunoglobulin gene(s) of interest. Preferred selectable markers include genes that confer resistance to drugs, such as neomycin, kanamycin, methotrexate and mycophenolic acid. The selectable marker may be an amplifiable selectable marker. Selectable markers are reviewed in Thilly, *Mammalian Cell Technology*, Butterworth Pub., Stoneham, Mass. Selectable markers may be introduced into the cell on the same plasmid as the gene(s) of interest or on a separate plasmid. See generally, U.S. Pat. No. 4,634,665, incorporated herein by reference. If on the same plasmid the selectable marker and the gene of interest may be under the control of the same or different promoters.

In other aspects the invention provides monoclonal antibodies, recombinant monoclonal antibodies, single polypeptide binding molecules, and the binding fragments thereof coupled to molecules which are cytotoxic for prostate cells. Thus, the monoclonal antibody or binding fragment serves to target the coupled cytotoxic molecule to prostate cells for a desired therapeutic (or, in some cases, diagnostic) effect.

Among the cytotoxic molecules which can be targeted by the monoclonal antibodies of the invention are active chemotherapeutic agents, prodrugs, cytotoxic or inhibitory peptides, cytokines, enzymes, and other monoclonal antibodies or binding fragments thereof, including catalytic antibodies. The monoclonal antibodies, when of the IgG isotype, can be coupled to themselves to form homodimers and trimers and hence possess increased binding avidity in a manner similar to IgM molecules. Alternatively, the monoclonal antibodies may be conjugated to antibodies of other binding specificities, such as immune modulating antibodies and those which bind to T lymphocyte antigens, via chemical or recombinant means, to form heterodimers or hybrid (bi-specific) antibodies having a desired activity against prostate and other effector cells.

Examples of monoclonal antibody-radionuclide conjugates which can be used in therapy include antibodies coupled to radionuclides such as $^{131}I$, $^{90}Y$, $^{105}Rh$, $^{47}Sc$, $^{67}Cu$, $^{212}Bi$, $^{211}At$, $^{188}Re$, $^{109}Pd$, $^{47}Sc$, $^{212}Pb$, and $^{153}Sm$. and the like, as described in (Gansow, *Int. J. Rad Appl. Instrum. [B], Nucl. Med. Biol.* 18:369–381 (1991)), which is incorporated herein by reference.

Monoclonal antibodies of the invention can also be coupled to conventional chemotherapeutic agents to achieve substantially higher levels of the drug at the prostate or metastatic site. Accordingly, drugs which may possess prohibitive levels of toxicity to non-prostate tissue may be administered at lower levels when conjugated to monoclonal antibodies or binding fragments specific for prostate cells. Drugs which may be coupled to the antibodies for targeting include those which may be employed for advanced prostatic cancer, such as doxorubicin, cyclophosphamide, cisplatin, adriamycin, estramustine, fluorouracil, ethinyl estradiol, mitoxantrone, methotrexate, finasteride, taxol, and megestrol. Methods of coupling may be direct via covalent bonds, or indirect via linking molecules, and will generally be known in the art for the particular drug selected. See, e.g., Thorpe et al., *Immunological Rev.* 62:119–158 (1982), which is incorporated herein by reference. The drugs may also be enclosed in liposomes which are then targeted to the prostate tumor sites by the monoclonal antibodies of the invention which are incorporated into the liposome membranes. A wide variety of methods for preparing liposomes filled with anticancer drugs and which are targeted by monoclonal antibodies to tumor sites are generally known, and are described in, for example, U.S. Pat. Nos. 4,235,871, 4,501,728, 4,837,028, 4,957,735 and 5,019,369, each of which is incorporated herein by reference.

In another method the drug may be a prodrug and the monoclonal antibody of the invention is coupled to an enzyme which converts the prodrug to more active drug at the prostate tumor site(s). In this method a monoclonal antibody of the invention, such as PR1, for example, is linked to an enzyme which is capable of converting a prodrug that is less cytotoxic to tumor cells than the parent drug, into the more active parent drug. When introduced into the host the antibody component of the conjugate directs the conjugate to the site of the prostate cells, including those at metastatic sites, and binds to the prostate cells. A prodrug that is a substrate for the enzyme is then introduced into the host and is converted by the enzyme at the tumor site into an active cytotoxic drug. Because in this method the drug is not bound to the antibody, the amount of drug capable of being delivered to the tumor cell site is not limited by the number of drug molecules that can be coupled to an antibody. Further, the number of active drug molecules at the tumor site is amplified because the antibody-bound enzyme of the conjugate can undergo numerous substrate turnovers, repeatedly converting prodrug into active drug. Representative drugs and enzymes useful in this method are discussed in U.S. Pat. No. 4,975,278, which is incorporated herein by reference in its entirety, and include cyclophosphamide, cisplatin and cisplatin analogues, fluorouracil, etc.

The monoclonal antibodies of the invention may also be employed to target hormonal agents and biological response modifiers useful in inhibiting growth or metastases of prostate cells, such as estradiol, diethylstilbestrol, alpha interferon, the nonapeptide leuprolide, goserelin, buserelin and other synthetic analogues of LHRH or nonsteroidal androgen antagonists, such as flutamide.

Other cytotoxic binding proteins of the invention are produced by fusing a cytotoxic domain and antigen binding domain derived from the monoclonal antibodies of the invention. A variety of cytotoxic molecules are suitable for use as the cytotoxic domain in the immunotoxins described here. Any toxin known to be useful as the toxic component of an immunotoxin may be used, preferably a protein toxin that may be recombinantly expressed. Particularly useful as the cytotoxic domain are bacterial toxins such as Pseudomonas exotoxin A (PE), diphtheria toxin, shiga toxin and shiga-like toxin, and ribosome inactivating toxins derived from plants and fungi, including ricin, α-sarcin, restrictotocin, mitogellin, tricanthosin, saporin-G, saporin-1, momordin, gelonin, pokeweed antiviral protein, abrin, modeccin and others described in *Genetically Engineered Toxins*, ed. A. Frankel, Marcel Dekker, Inc. (1992), incorporated by reference herein; and any recombinant derivatives of those proteins. See generally, Olsnes and Pihl, *Pharmac. Ther.* 25:355–381 (1982) and U.S. Pat. Nos. 4,675,382 and 4,894,443 which describe fusion proteins containing diphtheria toxin fragments, each incorporated by reference herein. Also useful as cytotoxic agents coupled to or otherwise targeted by the monoclonal antibodies of the invention are mammalian derived (preferably human) proteins with ribonucleolytic activity, such as ribonucleases engineered to be potent cytotoxins, and mammalian derived angiogenin, as described in co-pending commonly owned application Ser. No. 07/510,696, which is incorporated herein by reference.

The toxin molecules may be fused to, or otherwise bound to a monoclonal antibody of the invention or antigen binding domain thereof by methods generally known and available to those in the art. The two components may be chemically bonded together by any of a variety of well-known chemical procedures. For example, the linkage may be by way of heterobifunctional cross-linkers, e.g. SPDP, carbodiimide, glutaraldehyde, or the like. The toxin molecules may also be fused to the antibody or binding regions thereof by recombinant means, such as through the production of single chain antibodies. The genes encoding protein chains may be cloned in cDNA or in genomic form by any cloning procedure known to those skilled in the art. See for example Sambrook et al., *Molecular Cloning: A Laboratory Manual*, Cold Spring Harbor Laboratory Press, Cold Spring Harbor, N.Y. (1989). The recombinant production of various immunotoxins is well-known within the art and can be found, for example in Thorpe et al., *Monoclonal Antibodies in Clinical Medicine*, pp. 168–190 Academic Press, NY (1982), Waldmann, *Science*, 252:1657 (1991), and Pastan et al., *Ann. Rev. Biochem.* 61:331–354 (1992)) each of which is incorporated herein by reference.

In preferred embodiments the toxin is PE and derivatives thereof, and may be coupled to or fused via recombinant DNA techniques to a monoclonal antibody or binding domain which binds prostate cell associated antigen. To couple the toxin to the antibody, a form of the PE molecule with cysteine at amino acid position 287 can be used to couple to the antibody through the thiol moiety of cysteine. To produce recombinant PE-antigen binding molecules of the invention, it is desirable to insert the $V_L$ and $V_H$ binding regions from a monoclonal antibody of the invention, e.g., PR1, at a point within domain III of the PE molecule, most preferably fused between about amino acid positions 607 and 604 of the PE molecule. Alternatively, the antibody binding regions which recognize the prostate cell antigen may be inserted in replacement for PE domain Ia, i.e., the PE cytotoxic domain to be combined with the monoclonal antibody binding domain has domain Ia deleted, as has been described in commonly assigned Ser. No. 07/865,722 and 07/522,563, each of which is incorporated by reference.

PE proteins for use in the invention may be altered to have differing properties of affinity, specificity, stability and toxicity that make them particularly suitable for various clinical or biological applications. For example, deletions or changes may be made in PE or in a linker such as an IgG constant region connecting an antibody gene to PE, in order to increase cytotoxicity of the fusion protein toward target cells, or to decrease nonspecific cytotoxicity toward cells without the corresponding prostate antigen. Deleting a portion of the amino terminal end of PE domain II increases cytotoxic activity, in comparison to the use of native PE molecules or those where no significant deletion of domain II has occurred, as described in the commonly assigned Ser. No. 07/459,635 and 07/522,182, both of which are incorporated herein by reference. Other modifications include an appropriate carboxyl terminal sequence to the recombinant PE molecule to help translocate the molecule into the cytosol of target cells. Amino acid sequences which have been found to be effective include, REDLK (as in native PE), REDL or KDEL, repeats of those, or other sequences that function to maintain or recycle proteins into the endoplasmic reticulum. See, for example, Chaudhary et al., *Proc. Natl. Acad. Sci. USA* 87:308–312 (1990) and Seetharam et al., *J. Biol. Chem.* 266: 17376–17381 (1991), incorporated by reference herein, and Ser. No. 07/459,635.

The monoclonal antibodies and recombinant preparations thereof which bind to the human prostate cell antigen identified by monoclonal antibody PR1 and reacts strongly with prostate cancers, benign prostate hypertrophy and normal prostate cells may be employed in pharmaceutical compositions for a variety of therapeutic and diagnostic uses, such as the targeted therapy of metastatic prostate cancer, to deliver radioisotopes, drugs or toxins to prostate cancer cells for therapeutic or diagnostic purposes, etc.

Accordingly, the pharmaceutical compositions of the invention are intended for parenteral, topical, oral, or local administration for prophylactic and/or therapeutic treatment or for *in vivo* diagnostic use. Preferably, the pharmaceutical compositions are administered parenterally, i.e., intravenously, subcutaneously, or intramuscularly. Thus, this invention provides compositions for parenteral administration which comprise a solution of a monoclonal antibody of the invention or binding fragment thereof dissolved in a pharmaceutically acceptable carrier, preferably an aqueous carrier. A variety of aqueous carriers may be used, e.g., water, buffered water, 0.9% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such an pH adjusting and buffering agents, tonicity adjusting agents and the like, for example, sodium acetate, sodium lactate, sodium chloride, potassium chloride, calcium chloride, etc.

The concentration of the monoclonal antibody which binds to the prostate specific membrane antigen recognized by the PR1 antibody in these formulations can vary widely, i.e., from less than about 0.5%, usually at or at least about 1% to as much as 15 or 20% by weight and will be selected primarily by fluid volumes, viscosities, etc., in accordance with the particular mode of administration selected. Actual methods for preparing parenterally administrable compounds will be known or apparent to those skilled in the art and are described in detail in, for example, Remington's Pharmaceutical Science, 17th ed., Mack Publishing Company, Easton, Penna. (1985), which in incorporated herein by reference.

Determination of an effective amount of monoclonal antibody or conjugate thereof of the invention sufficient to inhibit growth of the prostate cells may be determined by, for example, monitoring metastatic sites with a variety of procedures, e.g., *in vivo* imaging or *ex vivo* diagnostic techniques, as described herein. Other prostate cancer markers may also be used to monitor therapy with the monoclonal antibodies of the invention, e.g., the PSA assay, which is commercially available.

The therapeutic compositions of the invention are administered to a patient already suffering from abnormal growth of prostate cells, e.g., benign prostate hyperplasia or prostate cancer, as described herein, in an amount sufficient to cure or at least partially arrest the disease. An amount adequate to accomplish this is defined as "therapeutically effective dose." Amounts effective for this use will depend on the severity of the disease and its location, particularly when a metastatic site is implicated, and the weight and general state of the patient being treated, but generally range from about 0.01 mg/kg to about 100 mg/kg host body weight of monoclonal antibody per day, with dosages of from about 0.1 mg/kg to about 10 mg/kg per day being more commonly used. Maintenance dosages over a prolonged period of time may be adjusted as necessary. It must be kept in mind that the materials of the present invention may be employed in serious disease states, that is, life-threatening or potentially life threatening situations. In such cases, in view of the minimization of extraneous substances and general lack of immunogenicity when a substantially human monoclonal antibody of the invention is employed to treat human hosts, it is possible and may be felt desirable by the treating physician to administer substantial excesses of these compositions.

Single or multiple administrations of the compositions can be carried out with the dose levels and pattern being selected by the treating physician. In any event, the pharmaceutical formulations should provide a quantity of the monoclonal antibody composition of the invention sufficient to effectively inhibit the prostate associated disease.

For the treatment of prostate cancer the pharmaceutical compositions of the present invention may be administered alone or as adjunct therapy. The compositions may be administered with, e.g., taxol, endocrine therapy, etc. When administered as adjunct therapy, the compositions of the present invention may be administered in conjunction with the other treatment modalities, or separately at different intervals.

The monoclonal antibodies and conjugates thereof can also be used in methods of *ex vivo* therapy. By *ex vivo* therapy is meant that therapeutic manipulations are performed outside the body. For example, bone marrow or other target cells or tissues are removed from a patient and treated with high doses of compositions which comprise the monoclonal antibodies of the invention, conjugated to cytotoxic agents such as toxins, drugs, labels, etc., proving a therapeutic concentration of the compositions far in excess of levels which could be accomplished or tolerated by the patient. Following treatment to eliminate the prostatic cells in the target cell population or tissue, the cells or tissues are return to the patient.

In another aspect of the invention, metastases of malignant prostate cells beyond the prostate organ can be detected by diagnostic imaging. By associating an imageable label with the monoclonal antibodies of the invention or binding fragments thereof, an image of the sites of metastases may be obtained. The images may be used for detection of prostatic metastases, in evaluating and monitoring therapy, and in guiding surgical removal of metastatic sites.

The method of imaging tissue sites of prostatic cell metastases comprises labeling a monoclonal antibody of the invention capable of binding to an antigen of the prostatic cell membrane. In one aspect, the labeled monoclonal antibody is then infused or injected into a patient, and the tissue sites are then imaged and the presence of prostatic carcinoma metastases determined. Conventional diagnostic imaging techniques may be employed, as are generally known in the art. Briefly, a monoclonal antibody of the invention is labeled, such as a radiolabel, and administered to a patient in an amount sufficient to deliver an adequate supply of labeled monoclonal antibody (or binding fragment thereof) to the targeted tissues so as to permit an image to be generated. The radiolabel provides the imaging input, while the coupled (labeled) monoclonal antibody provides the targeting capability of the radiolabeled unit. Among the various tissues appropriate for imaging, in addition to total body imaging, are those most likely to be sites of prostatic carcinoma metastases, e.g., lymph nodes, particularly of the pelvic area, bone marrow, bone, brain, liver, lung, or adrenal gland.

The labeling of the monoclonal antibody or binding fragment can be accomplished by covalently or noncovalently linking the antibody to a moiety which generates an input for imaging techniques. Exemplary labels useful in the present invention are radionuclides. Labeling may be performed by conventional techniques, including via chelating compounds, as described in, e.g., U.S. Pat. Nos. 4,741,900 and 4,986,979, which are incorporated by reference herein. Radionuclides useful in the present invention include gamma-emitters, positron emitters and fluorescence emitters. Exemplary radionuclides are known in the art and include $^{111}$In, $^{123}$I, $^{125}$I, $^{130}$I, $^{131}$I, $^{133}$I, $^{135}$I, $^{128}$Ba, $^{47}$Sc, $^{99}$Tc, $^{72}$As, $^{72}$Se, $^{90}$Y, $^{88}$Y, $^{97}$Ru, $^{100}$Pd, $^{109}$Pd, $^{105}$Rh, $^{198}$Au, $^{113}$Ag, $^{111}$Ag, $^{197}$Hg, $^{203}$Pg, $^{212}$Pb, $^{67}$Ga, $^{68}$Ga, $^{64}$Cu, $^{67}$Cr, $^{97}$Ru, $^{75}$Br, $^{76}$Br, $^{11}$C, $^{13}$N, $^{15}$O and $^{18}$F.

Once labeled, the monoclonal antibody is infused into a patient whose tissues are to be imaged. The infusion may be by any means suitable to deliver the labeled monoclonal antibody to the bloodstream of the patient, such as intraarterial, intravenous, intraperitoneal, subcutaneous, etc. The mode of administration is usually chosen according to the projected ultimate destination of the label. Such infusions may be given as single or multiple injections.

The labeled monoclonal antibody of the invention may be given in a pharmaceutical composition. Typically the labeled monoclonal antibody will be dispersed in a pharmaceutically acceptable carrier, such as, e.g., physiological saline or a physiologically acceptable buffer solution, as described above.

The amount of the labeled monoclonal antibody specific for prostate cells which is administered to a patient for imaging will depend primarily on the size of the patient and the purpose of the administration. The patient's physiological condition and the tissue site to be imaged or treated, if known, may affect the amount of labeled agent necessary to obtain a usable image. Dosage of labeled agent may be readily determined by one of ordinary skill. A typical dose of radiolabeled monoclonal antibody is between about 1 and about 3000 mCi. In humans, a standard imaging dose will be from about 1 to about 50 mCi, with about 10 to about 30 mCi being typical.

The imaging may be performed by one of the commercially available imaging scanners. Visualization of sites of metastases may be obtained by planar or single photon emission computed tomographic scans. The time lapse between infusion of the labeled monoclonal antibody and scan or imaging will vary somewhat with the patient's characteristics, e.g., body weight and condition, administration route, the label used, etc., but typically a lapse between 3 and 144 hours is required to allow the labeled monoclonal antibody to migrate to the target tissue and to clear from the uninvolved tissue. An appropriate time lapse can readily be determined by the worker skilled in diagnostic imaging. The imaging can be used as a guide to surgery or further therapy.

In another aspect, the present invention provides methods for diagnosing the presence of prostatic cells in a cellular sample obtained from a patient, i.e., *ex vivo* diagnosis. The sample will generally be obtained from a tissue that does not normally contain prostatic cells but are sites of possible prostatic carcinoma metastases, e.g., lymph nodes, bone marrow, etc. The samples, which may be obtained via biopsy, needle aspiration, and the like, are reacted with a monoclonal antibody of the present invention or a binding fragment thereof. The monoclonal antibody may be directly labeled, or may be labeled indirectly by the use of a labeled binding reagent specific for the monoclonal antibody, e.g., if the monoclonal antibody used to react with the sample is murine, a labeled goat immunoglobulin which binds murine immunoglobulin molecules may be employed. The label may be any of the readily known labels appropriate for *in vitro* diagnostic determinations, such as fluoresces, chemiluminescers, enzymes, radionuclides, dye particles, etc. Some suitable fluorophores include fluorescein, rhodamine, phycoerythrin, phycocyanin, and nile blue. Preferred luminescers include chemiluminescers, such as 3-(2'-spiroadamantane)-4-methoxy-4-(3"-phosphoryloxy)phenyl-1,2-dioxetane (AMPPD), luminol, or firefly luciferin. Among preferred enzymes are horseradish peroxidase (HRP), β-galactosidase (β-GAL), glucose oxidase, urease, β-lactamase, and alkaline phosphatase (AP). When the reporter label is an enzyme, the step of measuring may include exposing the bound complex to substrate and incubating for color, fluorescence or luminescence development. It will be evident to one skilled in the art that the particular substrate utilized will be dependent upon the enzyme chosen. Methods for coupling the label to the monoclonal antibody are dependent on the reporter, but such methods are generally known to the skilled artisan. Moreover, the immunoassays of the present invention can be performed in any of several configurations, which are reviewed extensively in *Enzyme Immunoassay*, E. T. Maggio, ed., CRC Press, Boca Raton, Fla. (1980); "Practice and Theory of Enzyme Immunoassays," P. Tijssen, *Laboratory Techniques in Biochemistry and Molecular Biology*, Elsevier Science Publishers B. V. Amsterdam (1985); and, Harlow and Lane, *Antibodies, A Laboratory Manual*, Cold Spring Harbor Laboratory Press, Cold Spring Harbor, N.Y. (1989), each of which is incorporated herein by reference.

Thus, in an exemplary assay for the diagnosis of metastatic prostate cancer, the monoclonal antibodies of the invention are added to a slide containing a 5 micron section of a biopsy specimen (for immunohistochemistry), or cells (for immunocytochemistry) from body fluid such as urine, cerebral spinal fluid, pleural effusion, etc. A series of linkers (e.g., biotinylated goat anti-mouse IgG followed by avidin DH:biotinylated horseradish peroxidase complex) and dyes (e.g., diaminobenzidine) are then added to the slides to detect binding of the monoclonal antibody, immunoreactive fragment or recombinant thereof to the prostate cells in the biopsy or body fluid by a color reaction. The amount of monoclonal antibody of the present invention used per slide and the incubation time can vary, but generally the IHC and ICC assays are conducted at room temperature for about 30 minutes using about 20 micrograms of monoclonal antibody. By this method prostate cells, including prostate carcinoma cells, can be detected in biopsy specimens and body fluids as an adjunct to making a diagnosis of cancer, or allow a differential diagnosis of prostate cancer and not another carcinoma.

The invention also provides kits for use with the compositions and methods of the present invention for the detection of prostatic cells in samples or tissues of interest. Thus, a monoclonal antibody of the invention, unbound or conjugated to a label, may be provided in a container or vial, in some instances in lyophilized form, either alone or in conjunction with additional reagents, such as buffers, stabilizers, biocides, inert proteins, e.g., serum albumin or the like. Frequently it will be desirable to include an inert extender or excipient to dilute the active ingredients, where the excipient may be present in from about 1 to 99% of the total composition. The kit may also contain instructions for using the components in the methods described herein.

The following experimental examples are offered by way of illustration, not by way of limitation.

EXAMPLE I

Isolation of Monoclonal Antibody PR1

This Example describes methods used for the immunization of animals with short term prostate cancer cell lines and the isolation of hybridoma PR1 producing a monoclonal antibody to a prostate cell associated antigen.

Balb/c mice were immunized intraperitoneally with a primary human prostate carcinoma cell strain using $5 \times 10^6$ cells/ml/mouse. The strain was cultured from a needle biopsy (Peehl et al., Prostate 19:141–147 (1991) derived from a cancer of Gleason Pattern 4+4. The cells were grown on collagen coated dishes in serum-free medium as previously described (Peehl et al., In Vitro 22:82–90 (1986) and Peehl, J. Tiss. Cult. Meths. 9:53–60 (1985)), scraped from the dishes and suspended in PBS. The mice were immunized on days 0, 5, 10 and 46. The fusion was performed on day 48 with Ag8.653 cells in accordance with fusion methods as previously described in Herzenberg et al., *Handbook of Exp. Immunol.* pp 25.1–25.7 (1979) and Goding, *Monoclonal Antibodies, Principles and Practice*, Academic Press, London, pp 59–93 (1985).

The antibody produced by each clone was screened by immunofluorescence on the short term prostate carcinoma cell strain that was used for immunization using a Screen Fast multiwell screening apparatus (Willingham, *Focus* 12:62–67 (1990)). Fifty-eight clones were identified that produced antibodies that were uniformly reactive with the surface of the immunizing cells. On the following day, the supernatants of these clones were screened by peroxidase immunohistochemistry on frozen sections of normal tissues and prostate carcinoma samples as described below.

Fresh frozen human tissues were obtained from the Cooperative Human Tissue Network (Columbus, Ohio), the National Disease Research Interchange (Philadelphia, Penna.), the Long Island Jewish Medical Center (New Hyde Park, N.Y.), the University of Alabama at Birmingham, Tissue Procurement Service (Birmingham, Ala.), Stanford Medical Center (Stanford, Calif.), the Medical University of South Carolina, Department of Pathology (Charleston, S.C.), and the Department of Urology, Wayne State University (Detroit, Mich.). Sections of these samples were cut using a cryostat (Haeker Inst. Inc., Fairfield, N.J.) at 5 μm thickness. The sections were thawed onto coverslips (#2:22× 22 mm) coated with Histostik (Accurate Chemical, Westbury, N.Y.), allowed to air dry, and then lyophilized overnight. All subsequent steps were carried out at room temperature. The sections were fixed in 100% acetone for 10 min, air-dried and then rehydrated in PBS (Dulbecco's PBS without calcium or magnesium) for 10 min. The sections were then incubated for 5 min in 10% normal goat serum in PBS, followed by two washes in PBS, and then incubated with 100 μl of the undiluted hybridoma culture supernatant for 1 hr or with a nonreactive control mouse monoclonal antibody (10 μg/ml in 2–4 mg/ml normal goat globulin, 0.1% saponin, 1 mM EGTA, PBS (NGG-Sap-PBS) as described in Pastan et al., *Cancer Res.* 51:3784–3787 (1991). Afterwards, the sections were washed thoroughly in PBS and incubated for 10 min in NGG-Sap-PBS followed by a 1 hr incubation with 25 mg/ml affinity purified goat anti-mouse IgG (H and L) conjugated to horseradish peroxidase (Jackson ImmunoResearch: Avondale, Penna., Cat #115-33562) in NGG-Sap-PBS with 5% AB Human Serum (Calbiochem; Somerville, N.J.). The sections were then washed with PBS, followed by a 10 min incubation in NGG-Sap-PBS, another PBS wash and then incubated with 0.5 mg/ml 3,3'diaminobenzidine (Sigma; St. Louis, Mo.) in PBS with 0.01% $H_2O_2$ for 10 min. After several washes in PBS, the sections were stained with Gills hematoxylin #1 (Fisher Chemical; Fair Lawn, N.J.) for 1–3 min followed by a $H_2O$ rinse and 1% $OsO_4$ (osmium tetroxide) for 1 min and then dehydrated in ethanol and xylene and mounted in Permount.

Among the supernants screened, only one clone, PR1, was found that preferentially reacted with the prostate tissues. Cell line PR1 was deposited with the American Type Culture Collection, 12301 Parklawn Dr., Rockville, Md. on Oct. 2, 1992 as ATCC No. HB11145.

Monoclonal antibody PR1 was determined to be an IgMk using the Immunoselect monoclonal antibody-based isotyping system for mouse immunoglobulins (Bethesda Research Labs, Gaithersburg, Md.).

To produce antibody from the PR1 cell line, cells from the antibody producing clone were grown to confluency and transferred to protein free medium (Ultradoma PF, Whittaker Bioproducts, Walkerville, Md.), $8 \times 10^8$ hybridoma cells in 100 ml of serum-free medium in each of 10 flasks. The supernatants were harvested every twenty-four hours on three consecutive days and clarified by centrifugation. The antibody was concentrated from the cell culture supernatant by precipitation with 60% ammonium sulfate (w/v) and the precipitate was resuspended in PBS and dialyzed against PBS overnight. The concentrated antibody was then purified over a TSK 250 gel filtration column (TosoHaas).

When analyzed by SDS-PAGE, the purified antibody showed only the light and heavy chain bands of the antibody. About 12 mg of pure antibody was obtained from the three liters produced by the three 24 hr harvests.

EXAMPLE II

Prostate Cell Specificity of PR1 Monoclonal Antibody

This Example describes the strong and uniform binding specificity of the PR1 monoclonal antibody for an antigen associated with normal and prostate cells and those from benign and metastatic prostate carcinoma, and having very weak reactivity with few cells of certain other normal human tissues.

A. Immunohistochemistry on normal and cancer specimens

The specificity of purified monoclonal antibody PR1 with normal human and cancer tissues was assessed by the same screening procedure described above except that 5 µg/ml of a nonreactive mouse monoclonal IgMk (13F5 from Dr. Kai Chang, NCI) in NGG-Sap-PBS was used.

The results of reacting monoclonal antibody PR1 with normal human tissues using frozen sections are summarized in Table I. Very strong reactivity was noted with normal prostate. Ten different samples were examined and all were strongly reactive. Strong reactivity was also noted with ten samples of benign prostatic hypertrophy. Some reactivity was noted with several other normal tissues, but the reactivity tended to be less strong than with prostate. In the kidney, a subset of collecting duct cells, the principal cells, were positive, where the antigen appeared to be on both the apical and basal surfaces of these cells. The antibody also reacted with cells of bile ducts that were seen in sections of the liver but not with hepatocytes, and with cells present in large ducts of the pancreas but not acinar cells.

TABLE I

Reactivity of Monoclonal Antibody PR1 with Normal Human Tissues

| Tissue | Reactivity |
| --- | --- |
| Adrenal | (−)(2/2) |
| Bladder | (−)(3/3) |
| Bone marrow | (−)(3/3) |
| Breast | (−)(1/1) |
| Cerebellum | (−)(5/5) |
| Colon | (+)(4/4) (weak + apical brush border) |
| Cerebal cortex | (−)(3/3) |
| Esophagus | (−)(3/3) |
| Heart | (−)(7/7) |
| Kidney | (+)(7/7) collecting duct/principal cell hetero. |
| Liver | (−) hepatocytes (5/5); (+ducts) (5/5) |
| Lung | (−)(2/2) |
| Lymph Node | (−)(2/2) |
| Pancreas | (−) acini and islets; (+ducts) (3/3) |
| Peripheral Nerve | (−)(1/1) |
| Pituitary | (− anterior lobe) (++pars intermedia) (−posterior lobe)(1/1) |
| Placenta | (−)(2/2) |
| Prostate | (++++)(10/10) |
| Prostate BPH | (++++)(10/10) |
| Salivary Gland | (+)(3/3) weakly + acini and ducts (3/3) |
| Skeletal Muscle | (−)(2/2) |
| Skin | (−)(3/3) |
| Spinal cord | (−)(2/2) |
| Spleen | (−)(2/2) |
| Small bowel | (weakly + apical brush border) (2/5), (−)(3/5) |
| Mesothelium (GI tract) | (−)(1/1) |
| Stomach | (weakly + parietal cells, hetero.) (3/3) |

TABLE I-continued

Reactivity of Monoclonal Antibody PR1 with Normal Human Tissues

| Tissue | Reactivity |
| --- | --- |
| Testes | (−)(1/1) |
| Thyroid | (−)(3/3) |
| Tonsil | (−)(1/1) |

In the stomach, the antibody reacted very weakly with parietal cells; it also reacted very weakly with colonic epithelium. Reactivity with the epithelium of the small bowel was mixed. Three samples did not react at all but two others reacted with weak, variable reactivity. This variability was seen even in samples from different regions of the small intestine from the same patient. Weak reactivity was also detected in the parotid gland and the pars intermedia lobe of the pituitary. No reactivity was detected with other normal tissues including the cerebral cortex and the cerebellum.

The results of monoclonal antibody PR1 reactivity on 26 separate samples of adenocarcinoma of the prostate are shown in Table II. With almost all the samples, monoclonal antibody PR1 reacted strongly and uniformly with all of the cancer cells. In only one sample was no reactivity detected. These cancer samples varied widely in their grade of malignancy. In addition, one sample which contained a lymph node metastases and one that had a bladder metastasis were found to be strongly positive. There was little or no reactivity with several other types of cancer including bladder, breast, ovary and colon cancer. These results indicate that monoclonal antibody PR1 recognizes a differentiation antigen present on the surface of normal prostate cells which continues to be expressed in almost all primary prostate cancers as well as in benign prostatic hypertrophy.

TABLE II

| Tissue Histology | PR-1 Reactivity[a] |
| --- | --- |
| Normal Prostate | ++ to ++++ (10/10) |
| Benign Prostatic Hypertrophy | ++ to ++++ (10/10) |
| Well-Differentiated Adenocarcinomas | + to ++++ (8/8) |
| Poorly-Differentiated Adenocarcinoma | + to ++++ (12/13)[b] |
| Unclassified Adenocarcinoma | ++ to ++++ (5/5) |

[a]Reactivity was assessed on a scale ranging from "−" negative) to "++++" (strongest reactivity).
[b]One poorly-differentiated tumor sample was negative.

Immunofluorescent examination of living cells

Cells were plated at $1 \times 10^4$ cells per dish and grown for two days in 35 mm diameter culture dishes. After washing with PBS, the cells were incubated with antibody at 4° C. in phosphate-buffered saline (PBS) containing 0.2% (w/v) bovine serum albumin (BSA). Primary mouse antibodies were used at 10–20 µg/ml in PBS-BSA with an incubation period of 30–60 min at 4° C. After washing in cold PBS, they were incubated with affinity-purified goat anti-mouse IgG (H+L) conjugated to rhodamine (25 µg/ml) in PBS-BSA at 4° C. for 30 min. After washing, the cells were fixed in 3.7% formaldehyde and mounted in situ under coverslips in buffered glycerol.

Monoclonal antibody PR1 reacted very strongly with the strain used to immunize the mice. The three human prostate cancer cell lines obtained from the American Type Culture Collection were also examined. No reactivity was noted with DU145 cells. The antibody reacted strongly with about 5% of the cells present in cultures of LNCaP cells, and less strongly with a few percent of cells present in PC3 cultures.

Antigen-positive LNCaP cells were enriched for antigen expression by fluorescence activated cell sorting (FACS, Fast Systems, Inc., Gaithersburg, Md.). Cells were washed in PBS in suspension at 4° C. After centrifugation cells were resuspended in PBS-BSA containing antibody PR1 at 10 μg/ml and incubated at 4° C. for 60 min. After washing in PBS, cells were incubated with affinity-purified goat anti-mouse IgG (H+L) conjugated to fluorescein (25 μg/ml) in PBS-BSA at 4° C. for 30 min. Cells were washed in PBS and sorted by FACS. Monoclonal antibody PR1 reacted strongly with about 40% of LNCaP cells that had been enriched by FACS using monoclonal antibody PR1. PR1 was also tested on several other cultured cell lines and did not show strong reactivity with any of these, although a low level of reactivity could not be excluded.

The suspicion that cell lines DU145, LNCaP and PC3 are not typical of cells present in prostate cancers as they grow in people is in part supported by the properties of monoclonal antibody PR1 which reacts strongly and uniformly with almost all adenocarcinomas of the prostate examined and 2/2 metastatic lesions. The PC-3 cell line, which was isolated from a primary grade IV adenocarcinoma, contains a small percentage of PR1 positive cells but most cells were PR1 negative. The LNCaP cell line, isolated from a metastatic lesion, also contains a small percentage of PR1 positive cells. However, cell line DU145, also isolated from a metastatic lesion was entirely unreactive with PR1.

Several features suggest that the antigen recognized by PR1 may be associated with carbohydrate. One of these is that the antibody reacted, although weakly, with salivary gland and small bowel, common reactive sites of anticarbohydrate antibodies.

EXAMPLE III

Production of Single-Chain PR1-PE Immunotoxin

This Example describes the cloning of cDNAs encoding the heavy and light chain variable regions of monoclonal antibody PR1, and the construction and characterization of the single-chain PR1-PE immunotoxin PR1(Fv)-PE38KDEL.

Cloning of cDNA encoding PR1 $V_L$ and $V_H$ and plasmid constructions

DNA fragments encoding the $V_H$ or $V_L$ of monoclonal antibody PR1 were obtained by PCR amplification of (random primed) reverse transcribed PR1-hybridoma RNA as described in Chaudhary et al., Proc. Natl. Acad. Sci. USA 87:1066–1070 (1990), which is incorporated herein by reference. $V_H$ cDNA was amplified with the primer pair PR1-H1: [5'CAGTRDCTRMAGGTGTCCATATGGATGTGCAGCTGGTGGAGTCTGG3'] [Seq. ID No. 5] and PR1-H2 [5'GGAGACAAGCTTGAAGACATTTGGGAAGGACTGACTC3'] [Seq. ID No. 6]. For $V_L$ cDNA was amplified with the primer pair: PR1-L1 [5'GTCTCCTCAGGCGGAGGGGGATCCGGTGGTGGCG GATCTGGAGGKGGCGGMAGCGAHRTTGTGATGACCCAGTCTCC3'] [Seq. ID No. 7] and PR1-L2 [5'AGTTGGTGCAGCATCAAAAGCTTTKAKYTCCAGCYT KGTGCC3'] [Seq. ID No. 8]. These primers contain NdeI, BamHI or HindIII sites (underlined) to facilitate cloning. The sequences of cloned PCR products were determined using a USB Sequenase kit.

To make a plasmid for expression of PR1(Fv) PE38KDEL, the DNA-fragments encoding PR1-$V_L$ and -$V_H$ were combined by PCR-splicing techniques (Chaudhary et al., supra) to code for a single chain Fv held together by a (gly4ser) 3 peptide linker. Amplification primers used for VL were L1 and L2, and for $V_H$ primer H1 was used but H2 (anneals to IgM CH1) was replaced by H3 [5'GGATCCCCTCCGCCTGAGGAGACGGTGACTGAGGTTCCT3,] [Seq. ID No. 9] which anneals to the 3'-end of the $V_H$ sequence and codes for a part of the linker. The PCR-fragment obtained after PCR-splicing (primers H1+L2) of fragments from separate $V_H$ and $V_L$ reactions (primers H1+H3, L1+L2) was cleaved with NdeI and HindIII to replace the B3(Fv) coding region of pULI9 (encoding B3(Fv)-PE38KDEL [C3]) to make pULI40 (see FIG. 1A). The construction of PE38KDEL in pULI9 is described in Brinkmann et al., Proc. Natl. Acad. Sci. USA 89:3075–3079 (1992) and pending U.S. patent application Ser. No. 07/767,331, each of which is incorporated herein by reference).

To confirm that the cloned cDNAs encoded the variable regions of PR1, a partial sequence was obtained of the amino terminus of the light chain from purified PR1 and found to be NH2-DIQMTQSPASLSA [Seq. ID No. 10]. This sequence was identical to the deduced protein sequence of the cloned $V_L$ DNA (FIG. 1A), except for a Gln to Val exchange of the third amino acid, which was introduced by the consensus PCR-primer. The amino terminal sequence of the PR1 heavy chain could not be obtained, probably because its amino terminus is blocked against Edman degradation. Therefore, RNA isolated from the PR1-producing hybridoma was directly sequenced, as described below.

Sequence analyses of the cloned cDNAs showed the light chain of PR1 to be kappa class V (Kabat et al., in Sequences of Proteins of Immunological Interest, U.S. Department of Health and Human Services, National Institutes of Health, Bethesda, Md. 5th ed. (1991)). It is almost identical to the light chain of the anti-idiotype monoclonal antibody A25.9.7 (Sablitzky and Rajewsky, EMBO J. 3:3005–3012 (1984)). The heavy chain variable region belongs to murine class 3B (Kabat et al., supra); it shows a remarkable similarity to monoclonal antibody K1 with only one major difference in CDR III (FIG. 1B). However, no cross reactivity between the two anticarcinoma antibodies was observed. Monoclonal antibody PR1 binds strongly to prostate tissues and carcinomas and not to OVCAR3 cells, and antibody K1 does not react with prostate cells but does react with many ovarian carcinomas, mesotheliomas, squamous cell carcinomas, and normal mesothelium (Chang et al., Int. J. Cancer 50: 373–381 (1992); Chang et al., Int. J. Cancer 51:548–554 (1992); and Chang et al., Amer J. Surg. Pathol. 16:258–268 (1992)), and strongly to OVCAR3 cells.

RNA-Sequencing

Direct sequencing of RNA was performed essentially as described by Geliebter et al., Proc. Natl. Acad. Sci. USA 83:3371–3375 (1986), using a $^{32}P$ radiolabeled primer (complementary to IgM CH1 coding sequences) to initiate polymerization. This technique excludes PCR-derived artifacts such as, e.g. selective amplification of only one of several DNA species. Five micrograms mRNA and 10 ng $^{32}P$-labeled primer (5'CATTTGGGAAGGACTGACTC3' [Seq. ID No. 11] complementary to murine IgM-CH1 sequence) were incubated in 15 μl of 250 mM KCl and 10 mM TrisHCl, pH 8, for 3 min at 80° C. followed by 1 hr. at 45° C. Three microliters of this RNA-primer annealing solution were added to a mixture of 2.5 μl chain elongation/termination mix, 1.5 μl 5× reverse transcriptase buffer and 0.5 μl (5u) AMV reverse transcriptase (elong/term. mix= ddNTP; solutions from USB sequenase kit, AMV-RT and 5× RT buffer from BRL) and incubated for 1 hr. at 50° C. Five microliters sequenase stop buffer were added, the samples boiled for 3 min and loaded on sequencing gels.

Only one sequence was obtained, representing the major species of heavy chain mRNA in monoclonal antibody PR1 producing cells. The sequence was identical to the sequence of cloned PR1($V_H$).

Expression of recombinant protein

Figure 3A:
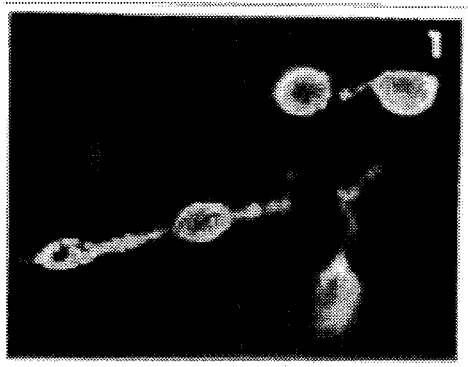
FIGS. 3-A, 3-B, 3-C, 3-D, 3-E and 3-F show the specific binding of PR1(Fv)-PE38KDEL to LNCaP cells enriched by sorting using immunofluorescence. Immunofluorescence of 10 µg/ml PR1(Fv)-PE38KDEL in (1) without competition, in (3) with 50 µg/ml of competing monoclonal antibody PR1, and in (5) with 50 µg/ml control IgM; (2), (4) and (6) are phase contrast pictures of the same fields used for fluorescence.
Figure 3B:
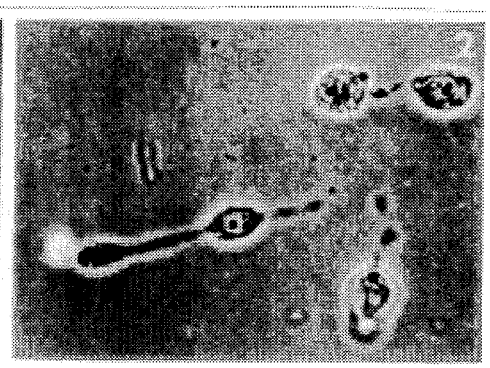
Figure 3C:
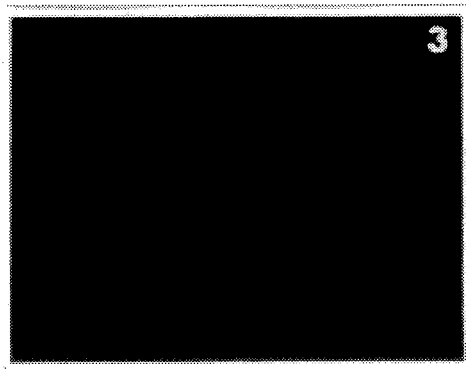
Figure 3D:
Figure 3E:
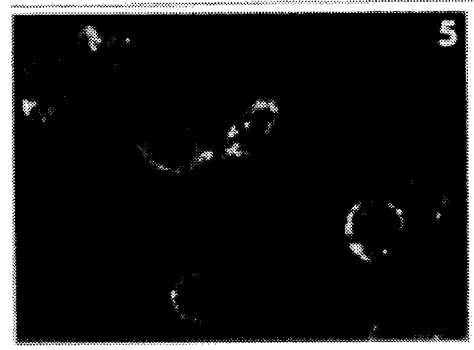
Figure 3F:
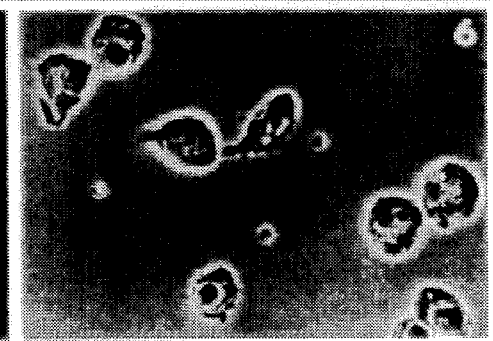

PR1(Fv)-PE38KDEL was produced in *E. coli* BL21 (λDE3) (Studier and Moffatt, *J. Mol. Biol.* 189:113–130 (1986)) containing pUL140 as described in Buchner et al., *Anal. Biochem.* 205:263–270 (1992). *E. coli* BL21 (λDE3) cells harboring the plasmid pUL140 (FIG. 2A) for expression of PR1(Fv)-PE38KDEL accumulated recombinant immunotoxin upon IPTG induction in intracellular inclusion bodies. Those inclusion bodies were isolated and the recombinant toxin solubilized, reduced and refolded to active immunotoxin by a "rapid dilution" method containing redox-shuffling and aggregation-preventing additives in the refolding buffer. Properly folded molecules were purified to near homogeneity by ion-exchange and size exclusion chromatography. The amount of recombinant protein in inclusion bodies, the purity of the inclusion bodies and composition of the final product after refolding and purification is shown in FIG. 3B.

EXAMPLE IV

Cytotoxicity of PR1-PE Immunotoxin For Prostate Cells

This Example demonstrates that the single-chain PR1-Pseudomonas exotoxin A immunotoxin binds to and is selectively cytotoxic towards a prostate carcinoma cell line enriched to express the PR1 antigen.

Although monoclonal antibody PR1 binds specifically to an antigen abundant on prostate cancers and normal prostate cells, the antigen is present in only a small proportion of cells from the cell line LNCaP and is not present on cell line DU145. Because it was difficult to assess the cytotoxic action of PR1(Fv)-PE38KDEL on cells of which only about 5% express the antigen, a fluorescence activated cell sorter (FACS) was used to enrich for PR1 positive cells.

PR1 positive LNCaP cells were enriched using a FACS according to Parks et al., *Experimental Immunology*, eds. Wehr, D. et al., (Blackwell Scientific), pp. 29.1–29.21. Whereas the original LNCaP sample had about 5% PR1 positive cells, after one cycle of FACS sorting, 20–40% of the LNCaP cells were strongly PR1 positive. These cells were then used for immunofluorescence and cytotoxicity experiments.

PR1 antigen expressing cells were also separated from antigen negative cells by means of antibody-coated magnetic beads (Padmanabhan et al., *J. Immunol.* 16:91–102 (1989)). Beads for isolation of PR1-expressing cells were prepared by overnight incubation of anti-mouse-IgM beads (Advanced Magnetics) with monoclonal antibody PR1 in PBS/0.1% BSA at 4° C. and subsequent washing (2×) in PBS/0.1% BSA. Beads for sorting of OVCAR3 cells were prepared by coating the anti-mouse-IgM beads with monoclonal antibody 13F5 (recognizing an antigen on OVCAR3), using the same conditions as for monoclonal antibody PR1. Cells were grown, incubated with beads and sorted in 25 cm² flasks (Costar 3025) as described in Padmanabhan et al., supra, with the modification that the cells were washed by gentle pipetting about twenty times to dissolve aggregates of live and dead cells when sorting samples for cytotoxicity assays.

Binding of PR1 and PR1(Fv)-PE38KDEL was detected by immunofluorescence as described above in Example II, using goat anti-mouse-Fab IgG-rhodamine for PR1 IgM and rabbit antiPE IgG and goat anti-rabbit IgG-rhodamine for PR1(Fv)-PE38KDEL. Immunoperoxidase localization of the antigen on frozen sections was performed as described in Example II.

The ability of PR1(Fv)-PE38KDEL to bind selectively to antigen expressing LNCaP cells is shown in FIG. 3. The binding was specific because it was displaced by excess monoclonal antibody PR1 at 50 μg/ml but not by a control IgM (monoclonal antibody 13F5). The signals observed with the recombinant immunotoxin were weaker than observed with equivalent concentrations of PR1, probably in part due to the differences in binding affinity between the polyvalent (IgM) and the monovalent (Fv). Cell lines that did not bind monoclonal antibody PR1 also gave no fluorescent signal with the recombinant immunotoxin (Table 3).

The toxicity of PR1(Fv)-PE38KDEL was examined on several carcinoma cell lines by the ability to inhibit protein synthesis. This was determined in 96-well plates according to the general procedure of Brinkmann et al., *Proc. Natl. Acad. Sci. USA* 88:8616–8620 (1991). For competition of cytotoxicity, 15 μg of monoclonal antibody PR1 or 13F5 was added 15 min prior to addition of toxin. Alternatively, the assays were combined with cell-sorting with antibody-coated magnetic beads.

Figure 4A:
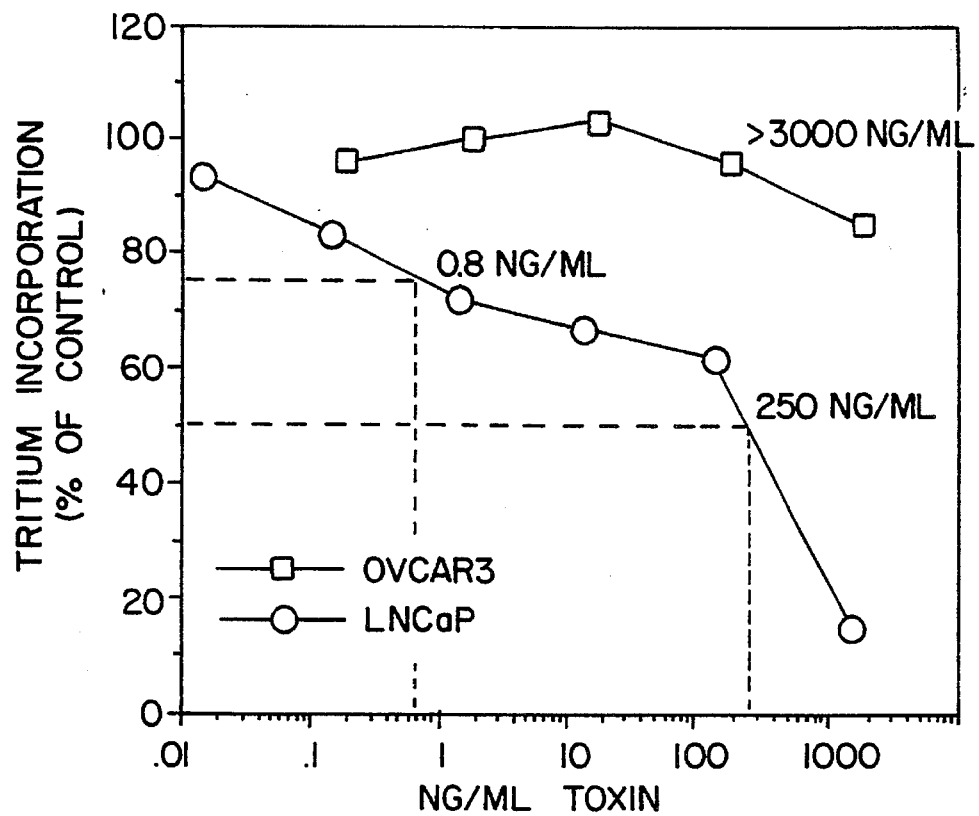
FIG. 4A shows the biphasic cytotoxicity of PR1(Fv)-PE38KDEL towards a mixed population of the LACaP cell line.
Figure 4B:
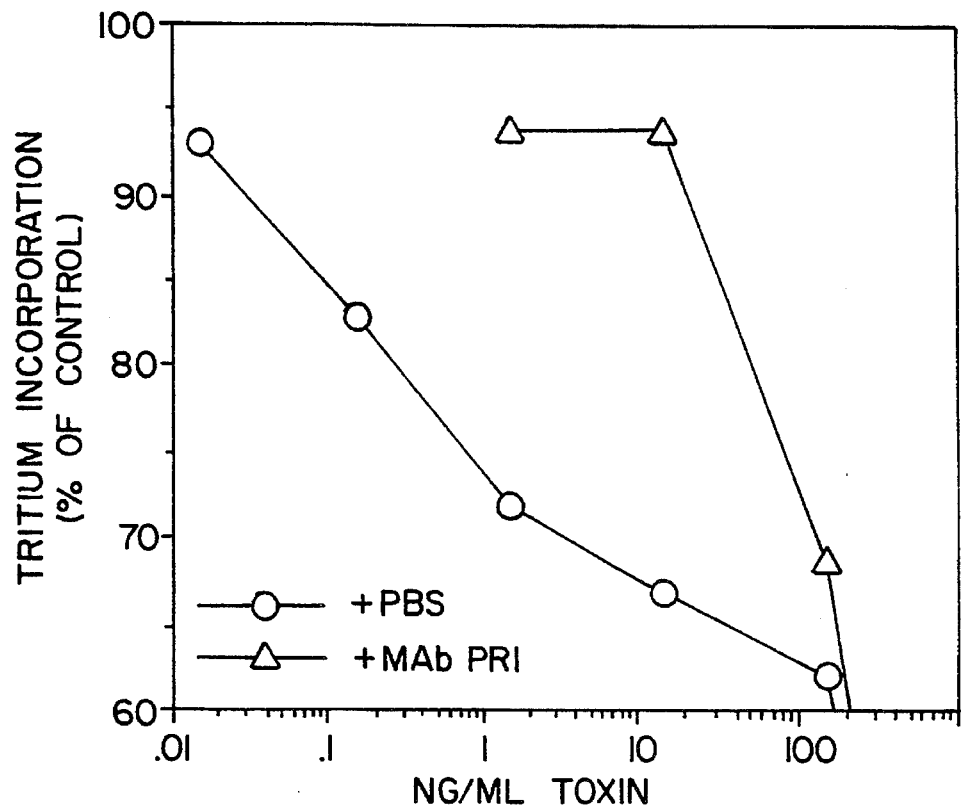
FIG. 4B is the competition of toxicity of PR1(Fv)-PE38KDEL by monoclonal antibody PR1 (IgM) on PR1-positive LNCaP cells.

FIG. 4 and Table III show the cytotoxic effect of the recombinant immunotoxin towards monoclonal antibody PR1 positive LNCaP cells (enriched by FACS to obtain a population composed of about 40% strongly antigen positive cells; the rest contained very little or no detectable antigen when analyzed by immunofluorescence with PR1). Using these enriched LNCaP cells, the cytotoxicity curve was biphasic. About 40% of the cells were very sensitive to the recombinant immunotoxin, with an ID$_{50}$ of about 0.8 ng/ml. The other 60% were more resistant (ID$_{50}$ about 250 ng/ml). The cytotoxic effect of PR1(Fv)-PE38KDEL was specific because excess PR1 (15 μg/ml) blocked the cytotoxic effect but a control IgM (13F5) did not (FIG. 3). Furthermore, antigen negative cells such as the ovarian cancer cell line OVCAR3 were not affected by the recombinant immunotoxin (Table III).

TABLE III

Specificity and cytotoxicity of PR1(Fv)-PE38KDEL.

| | | | PR1(Fv)-PE38KDEL | |
| --- | --- | --- | --- | --- |
| Cell Line | Carcinoma | PR1-binding | Binding | ID$_{50}$(ng/ml) |
| LNCaP | prostate | +++(het) | +(het) | 0.8 (250) |
| OVCAR3 | ovarian | – | – | >1000 |
| KB | epidermoid | – | n.d. | >1000 |

The ID$_{50}$ is the concentration of toxin that reduces protein synthesis of cells by 50%. (het) heterogenous immunofluorescence staining pattern; about 20–40% of the cells were strongly positive (ID$_{50}$ = 0.8 ng/ml) and 60% were weak or negative (ID$_{50}$ = 250 ng/ml).

Figure 5:
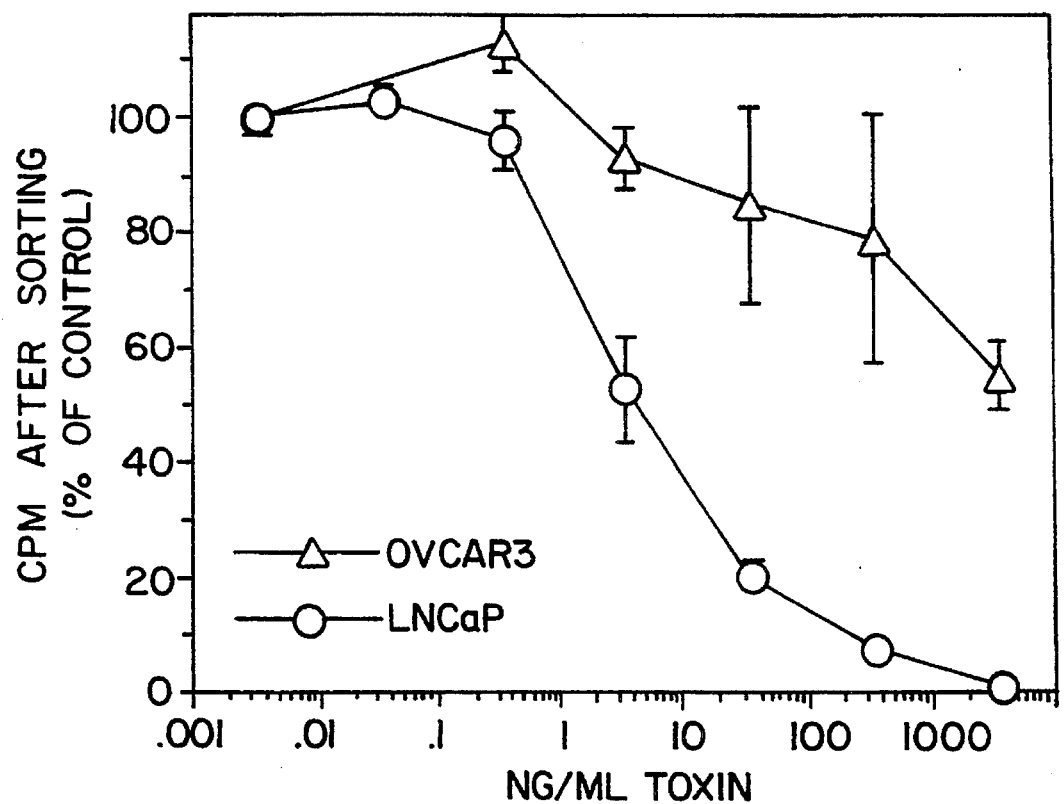
FIG. 5 shows the specificity of PR1(Fv)- PE38KDEL towards PR1-antigen expressing LNCaP cells, determined by sorting with antibody-coated magnetic beads.
Figure 2B:
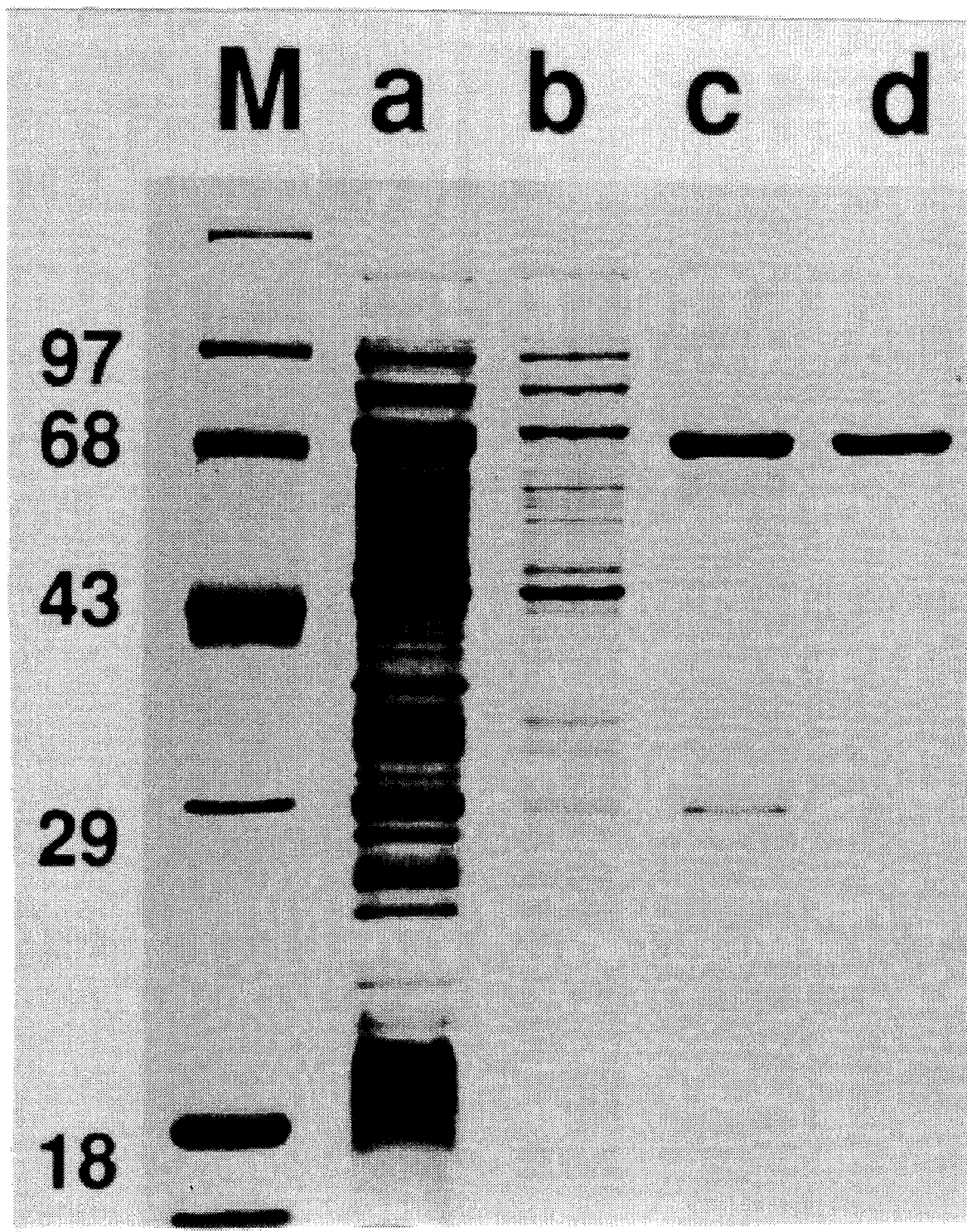

To assess whether the recombinant PR1(Fv)-immunotoxin could specifically eliminate antigen positive cells from a mixed population of cells, LNCaP cultures (immunofluorescence with PR1 had shown about 10% of the cells expressed the PR1 antigen) were incubated with different concentrations of immunotoxin for 40 hrs. The cultures were then radiolabeled for 5 hrs with ³H-leucine and remaining antigen expressing cells were isolated with PR1-labeled magnetic beads. FIG. 5 shows that PR1(Fv)-PE38KDEL was very cytotoxic towards PR1-expressing LNCaP cells. The ID$_{50}$ was about 3 ng/ml (the mean of four experiments). When antigen negative OVCAR3 control cells were sorted in the same manner with OVCAR3 specific 13F5(IgM)-coated beads, they were not affected. The cytotoxicity of PR1(Fv)-PE38KDEL towards LNCaP prostate carcinoma cells was specific because the cytotoxicity of the recombinant toxin was competed by addition of excess monoclonal antibody PR1.

Thus, the single chain immunotoxin PR1(Fv)-PE38KDEL bound prostate cells with the same specificity as the monoclonal antibody PR1, and its binding could be competed by monoclonal antibody PR1, confirming that the antigen recognized was the same. However, immunofluorescence signals with PR1(Fv)-PE38KDEL were slightly decreased when compared with monoclonal antibody PR1 (IgM). The reduced binding probably reflects, at least in part, the difference between monovalent (Fv) and multivalent (IgM) binding. Lower immunofluorescence signals with Fab-fragments obtained by proteolytic digestion of PR1 were in accordance with this conclusion. In addition, the presence of an N glycosylation sequence (NYT) in CDR2 of PR1VH (FIG. 1A) indicates that PR1 (IgM) might be glycosylated. It has been shown that glycosylation of the CDRs of antibodies can contribute to antigen binding (Walfick et al., J. Exp. Med. 168:1099–1109 (1988)). Because proteins from E. coli are not glycosylated, the recombinant immunotoxin may have reduced binding and activity.

Thus, as shown above, PR1(Fv)-PE38KDEL is selectively toxic to LNCaP carcinoma cells expressing the PR1 antigen. The $ID_{50}$ of PR1(Fv)-PE38KDEL on antigen positive cells was between 0.8 and 3.0 ng/ml. Immunotoxins with this activity level have been found to cause complete regression of other antigen positive tumors in mice (Brinkmann et al., Supra). Because the PR1 antigen is strongly expressed in prostate carcinomas and normal prostate, but only in few other normal tissues, PR1(Fv)-PE38KDEL can be used in humans for treatment of prostate cancer.

It is evident from the above results that the subject invention provides monoclonal antibodies and compositions which are specific for an antigen associated with a large majority of prostate cells, including those cells associated with prostate cancers. Accordingly, the invention provides new methods for the treatment of prostate cancer, as exemplified by the cytotoxic activity of the immunotoxin formed by joining the single chain PR1 to Pseudomonas exotoxin, and new methods for the diagnosis of prostate cancer.

All publications and patent applications mentioned in this specification are indicative of the level of skill of those skilled in the art to which this invention pertains. All publications, patents and patent applications are herein incorporated by reference to the same extent as if each individual publication, patent or patent application was specifically and individually indicated to be incorporated herein by reference.

From the foregoing it will be appreciated that, although specific embodiments of the invention have been described herein for purposes of illustration, various modifications may be made without deviating from the spirit and scope of the invention. Accordingly, the invention is not to be limited except as by the appended claims.

What is claimed is:

1. A monoclonal antibody which is the PR1 monoclonal antibody.

2. A monoclonal antibody or binding fragment thereof which competes with monoclonal antibody PR1 for binding to a prostate cell associated antigen and which contains VH and VL complementarity determining regions of monoclonal antibody PR1.

3. The monoclonal antibody of claim 2, in which the Fc region is human.

4. The monoclonal antibody of claim 3, in which the Fv framework is human.

5. The monoclonal antibody of claim 2, which is an IgG isotype.

6. A cell line which secretes a monoclonal antibody which competes with monoclonal antibody PR1 for binding to a prostate cell associated antigen and, which is ATCC No. HB 11145.

7. A method for screening for the presence of metastatic prostate cancer in an individual, comprising exposing cells or tissues of an individual to a monoclonal antibody or binding fragment thereof which competes with monoclonal antibody PR1 for binding to a prostate cell associated antigen and which containing VH and VL complementarity determining regions of monoclonal antibody PR1 and detecting the binding of the monoclonal antibody or binding fragment to the cells or tissue.

8. The method of claim 7, wherein the monoclonal antibody is labeled.

9. The method of claim 8, wherein the label is a radionuclide, fluorescer, enzyme or chemiluminscer.

10. The method of claim 7, wherein the cells or tissues are exposed in vivo to the monoclonal antibody.

11. The method of claim 7, wherein the cells or tissues are obtained from the patient and exposed to the monoclonal antibody in vitro under conditions conducive to immune complex formation.

* * * * *